US011617828B2

(12) United States Patent
Tong et al.

(10) Patent No.: US 11,617,828 B2
(45) Date of Patent: Apr. 4, 2023

(54) RESERVOIR CONNECTION INTERFACE WITH DETECTABLE SIGNATURE

(71) Applicant: Medtronic Minimed, Inc., Northridge, CA (US)

(72) Inventors: Davy Tong, Thousand Oaks, CA (US); An Thien Pham, Rosemead, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 702 days.

(21) Appl. No.: 16/514,495

(22) Filed: Jul. 17, 2019

(65) Prior Publication Data
US 2021/0015997 A1 Jan. 21, 2021

(51) Int. Cl.
*A61M 31/00* (2006.01)
*A61M 5/162* (2006.01)
*A61M 5/145* (2006.01)
*A61M 39/10* (2006.01)
*A61M 5/14* (2006.01)

(52) U.S. Cl.
CPC .......... *A61M 5/162* (2013.01); *A61M 5/1456* (2013.01); *A61M 39/10* (2013.01); *A61M 2005/1402* (2013.01); *A61M 2039/1072* (2013.01); *A61M 2205/14* (2013.01); *A61M 2205/3317* (2013.01);
(Continued)

(58) Field of Classification Search
CPC .... A61M 39/10; A61M 5/1456; A61M 5/162; A61M 2039/1044; A61M 2205/14; A61M 2205/3317; A61M 2205/6009; A61M 2205/6027; A61M 2205/6054; A61M 5/14566
See application file for complete search history.

(56) References Cited

U.S. PATENT DOCUMENTS 4,755,173 A 7/1988 Konopka et al.
5,391,250 A 2/1995 Cheney et al.
(Continued)

FOREIGN PATENT DOCUMENTS

EP 2 155 288 A1 2/2010
EP 2 313 144 A1 4/2011
(Continued)

OTHER PUBLICATIONS

Brazilian Office Action dated Mar. 24, 2020, from application No. 112017001256-1.
(Continued)

*Primary Examiner* — Rebecca E Eisenberg
(74) *Attorney, Agent, or Firm* — Foley & Lardner LLP

(57) ABSTRACT

A connector interface system includes a cap to connect to a reservoir to form a reservoir/cap unit for installation into an infusion pump device. The cap has at least one receptacle for receiving one or more detectable features comprising at least one disc-shaped member, for detection by at least one sensor element on the infusion pump device when the reservoir of the reservoir/cap unit is received in a reservoir receptacle of the infusion pump device. The at least one detectable feature has at least one detectable parameter that is associated with one or more characteristics of the cap, the reservoir, the infusion pump device, a cannula associated with the cap or a tubing connected between the cap and the cannula.

17 Claims, 10 Drawing Sheets

(52) U.S. Cl.
CPC ............... *A61M 2205/6009* (2013.01); *A61M 2205/6027* (2013.01); *A61M 2205/6054* (2013.01)

(56) References Cited

U.S. PATENT DOCUMENTS

| | | | |
|---|---|---|---|
| 5,485,408 A | 1/1996 | Blomquist |
| 5,522,803 A | 6/1996 | Teissen-Simony |
| 5,602,472 A | 2/1997 | Bergstedt et al. |
| 5,665,065 A | 9/1997 | Colman et al. |
| 5,788,099 A | 8/1998 | Treu et al. |
| 5,800,420 A | 9/1998 | Gross et al. |
| 5,807,375 A | 9/1998 | Gross et al. |
| 5,925,021 A | 7/1999 | Castellano et al. |
| 5,954,643 A | 9/1999 | Vanantwerp et al. |
| 6,017,328 A | 1/2000 | Fischell et al. |
| 6,171,276 B1 | 1/2001 | Lippe et al. |
| 6,186,982 B1 | 2/2001 | Gross et al. |
| 6,246,992 B1 | 6/2001 | Brown |
| 6,248,067 B1 | 6/2001 | Causey et al. |
| 6,248,093 B1 | 6/2001 | Moberg |
| 6,355,021 B1 | 3/2002 | Nielsen et al. |
| 6,379,301 B1 | 4/2002 | Worthington et al. |
| 6,544,212 B2 | 4/2003 | Galley et al. |
| 6,558,351 B1 | 5/2003 | Steil et al. |
| 6,585,695 B1 | 7/2003 | Adair et al. |
| 6,591,876 B2 | 7/2003 | Safabash |
| 6,641,533 B2 | 11/2003 | Causey et al. |
| 6,656,157 B1 | 12/2003 | Duchon et al. |
| 6,736,797 B1 | 5/2004 | Larsen et al. |
| 6,749,587 B2 | 6/2004 | Flaherty |
| 6,766,183 B2 | 7/2004 | Walsh et al. |
| 6,801,420 B2 | 10/2004 | Talbot et al. |
| 6,804,544 B2 | 10/2004 | Van Antwerp et al. |
| 7,003,336 B2 | 2/2006 | Holker et al. |
| 7,029,444 B2 | 4/2006 | Shin et al. |
| 7,066,909 B1 | 6/2006 | Peter et al. |
| 7,137,964 B2 | 11/2006 | Flaherty |
| 7,303,549 B2 | 12/2007 | Flaherty et al. |
| 7,399,277 B2 | 7/2008 | Saidara et al. |
| 7,442,186 B2 | 10/2008 | Blomquist |
| 7,602,310 B2 | 10/2009 | Mann et al. |
| 7,647,237 B2 | 1/2010 | Malave et al. |
| 7,699,807 B2 | 4/2010 | Faust et al. |
| 7,727,148 B2 | 6/2010 | Talbot et al. |
| 7,785,313 B2 | 8/2010 | Mastrototaro |
| 7,806,886 B2 | 10/2010 | Kanderian et al. |
| 7,819,843 B2 | 10/2010 | Mann et al. |
| 7,828,764 B2 | 11/2010 | Moberg et al. |
| 7,879,010 B2 | 2/2011 | Hunn et al. |
| 7,890,295 B2 | 2/2011 | Shin et al. |
| 7,892,206 B2 | 2/2011 | Moberg et al. |
| 7,892,748 B2 | 2/2011 | Norrild et al. |
| 7,901,394 B2 | 3/2011 | Ireland et al. |
| 7,942,844 B2 | 5/2011 | Moberg et al. |
| 7,946,985 B2 | 5/2011 | Mastrototaro et al. |
| 7,955,305 B2 | 6/2011 | Moberg et al. |
| 7,963,954 B2 | 6/2011 | Kavazov |
| 7,967,785 B2 | 6/2011 | Morgan et al. |
| 7,977,112 B2 | 7/2011 | Burke et al. |
| 7,979,259 B2 | 7/2011 | Brown |
| 7,985,330 B2 | 7/2011 | Wang et al. |
| 8,024,201 B2 | 9/2011 | Brown |
| 8,100,852 B2 | 1/2012 | Moberg et al. |
| 8,114,268 B2 | 2/2012 | Wang et al. |
| 8,114,269 B2 | 2/2012 | Cooper et al. |
| 8,135,250 B1 | 3/2012 | Wach et al. |
| 8,137,314 B2 | 3/2012 | Mounce et al. |
| 8,181,849 B2 | 5/2012 | Bazargan et al. |
| 8,182,462 B2 | 5/2012 | Istoc et al. |
| 8,192,395 B2 | 6/2012 | Estes et al. |
| 8,195,265 B2 | 6/2012 | Goode et al. |
| 8,202,250 B2 | 6/2012 | Stutz, Jr. |
| 8,207,859 B2 | 6/2012 | Enegren et al. |
| 8,226,615 B2 | 7/2012 | Bikovsky |
| 8,257,259 B2 | 9/2012 | Brauker et al. |
| 8,267,921 B2 | 9/2012 | Yodfat et al. |
| 8,275,437 B2 | 9/2012 | Brauker et al. |
| 8,277,415 B2 | 10/2012 | Mounce et al. |
| 8,292,849 B2 | 10/2012 | Bobroff et al. |
| 8,298,172 B2 | 10/2012 | Nielsen et al. |
| 8,303,572 B2 | 11/2012 | Adair et al. |
| 8,305,580 B2 | 11/2012 | Aasmul |
| 8,308,679 B2 | 11/2012 | Hanson et al. |
| 8,313,433 B2 | 11/2012 | Cohen et al. |
| 8,318,443 B2 | 11/2012 | Norrild et al. |
| 8,323,250 B2 | 12/2012 | Chong et al. |
| 8,343,092 B2 | 1/2013 | Rush et al. |
| 8,352,011 B2 | 1/2013 | Van Antwerp et al. |
| 8,353,829 B2 | 1/2013 | Say et al. |
| 8,512,288 B2 | 8/2013 | Moberg et al. |
| 8,771,233 B2 | 7/2014 | Watanabe et al. |
| 9,452,255 B2 | 9/2016 | Tieck et al. |
| 9,517,299 B2 | 12/2016 | Tieck et al. |
| 9,744,290 B2 | 8/2017 | Tieck et al. |
| 2002/0173748 A1 | 11/2002 | McConnell et al. |
| 2003/0065287 A1 | 4/2003 | Spohn et al. |
| 2003/0120212 A1 | 6/2003 | Dedig et al. |
| 2004/0251896 A1 | 12/2004 | Mizutani et al. |
| 2005/0007104 A1 | 1/2005 | Lequesne et al. |
| 2005/0244493 A1 | 11/2005 | Withiam et al. |
| 2007/0073235 A1 | 3/2007 | Estes et al. |
| 2007/0100281 A1 | 5/2007 | Morris et al. |
| 2007/0123819 A1 | 5/2007 | Mernoe et al. |
| 2007/0167912 A1 | 7/2007 | Causey et al. |
| 2008/0021438 A1 | 1/2008 | Dacquay et al. |
| 2009/0317002 A1 | 12/2009 | Dein |
| 2010/0010443 A1 | 1/2010 | Morgan et al. |
| 2010/0137790 A1 | 6/2010 | Yodfat |
| 2010/0160861 A1 | 6/2010 | Causey et al. |
| 2010/0164727 A1 | 7/2010 | Bazargan et al. |
| 2010/0168670 A1 | 7/2010 | Srisathapat et al. |
| 2010/0168711 A1 | 7/2010 | Bazargan et al. |
| 2011/0004165 A1 | 1/2011 | Iio et al. |
| 2011/0137162 A1 | 6/2011 | Bruce et al. |
| 2011/0160655 A1 | 6/2011 | Hanson et al. |
| 2011/0224649 A1 | 9/2011 | Duane et al. |
| 2011/0257578 A1 | 10/2011 | Zanotti et al. |
| 2012/0101470 A1 | 4/2012 | Rasmussen et al. |
| 2012/0215094 A1 | 8/2012 | Rahimian et al. |
| 2012/0259282 A1 | 10/2012 | Alderete et al. |
| 2012/0323208 A1 | 12/2012 | Bochenko et al. |
| 2012/0330228 A1 | 12/2012 | Day et al. |
| 2013/0018356 A1 | 1/2013 | Prince et al. |
| 2013/0181538 A1 | 7/2013 | Calasso |
| 2013/0204227 A1 | 8/2013 | Bochenko et al. |
| 2013/0267894 A1 | 10/2013 | Woolford et al. |
| 2014/0018735 A1 | 1/2014 | Causey et al. |
| 2014/0103911 A1 | 4/2014 | Honda et al. |
| 2014/0276213 A1 | 9/2014 | Bochenko |
| 2015/0374907 A1 | 12/2015 | Morton |
| 2016/0015885 A1 | 1/2016 | Pananen et al. |
| 2016/0051742 A1 | 2/2016 | Strohhofer et al. |
| 2016/0120751 A1 | 5/2016 | Mounce et al. |
| 2017/0028124 A1* | 2/2017 | Deak ................ A61M 5/1684 |
| 2017/0333612 A1 | 11/2017 | Childers et al. |

FOREIGN PATENT DOCUMENTS

| | | |
|---|---|---|
| EP | 2 409 720 | 1/2012 |
| EP | 2 352 535 B1 | 9/2015 |
| JP | 2002-528234 A | 9/2002 |
| JP | 2010-532239 A | 10/2010 |
| WO | WO-2008/114218 A2 | 9/2008 |
| WO | WO-2010/037753 A1 | 4/2010 |
| WO | WO-2010/070799 A1 | 6/2010 |
| WO | WO-2017/123703 A2 | 7/2017 |

OTHER PUBLICATIONS

Final Office Action dated Mar. 24, 2020, from U.S. Appl. No. 14/801,429.

(56) References Cited

OTHER PUBLICATIONS

Final Office Action dated Mar. 25, 2020, from U.S. Appl. No. 14/801,548.
Final Office Action dated Oct. 22, 2020, from U.S. Appl. No. 14/801,429.
Indian Examination Report dated Oct. 2, 2020, from application No. 201617042366.
International Search Report and Written Opinion dated Oct. 9, 2020 for PCT Application No. PCT/US2020/041869.
Japanese Office Action for Application No. 2019-141925 dated Sep. 1, 2020 with English translation (7 pages).
Non-Final Office Action dated Sep. 9, 2020, from U.S. Appl. No. 14/801,266.
Canadian Examiner's Report dated Dec. 9, 2019, from application No. 3030922.
Final Office Action dated Mar. 6, 2020, from U.S. Appl. No. 14/801,266.
Australian Examination Report dated Aug. 13, 2019, from application No. 2018241148.
European Office Action dated Jul. 9, 2019, from application No. 15745670.8.
European Office Action dated Nov. 29, 2019, from application No. 15745670.8.
Final Office Action dated Jul. 18, 2018, from U.S. Appl. No. 14/801,429.
Final Office Action dated Jul. 19, 2018 from U.S. Appl. No. 14/801,266.
Final Office Action dated Jul. 19, 2018, from U.S. Appl. No. 14/801,548.
Final Office Action dated Jun. 6, 2019, from U.S. Appl. No. 14/801,548.
Final Office Action dated May 16, 2019, from U.S. Appl. No. 14/801,266.
Final Office Action dated May 17, 2019, from U.S. Appl. No. 14/801,429.
Final Office Action dated Nov. 2, 2018, from U.S. Appl. No. 14/801,338.
International Preliminary Report on Patentability dated Feb. 2, 2017, from related international application No. PCT/US2015/040974.
International Search Report and Written Opinion dated Dec. 1, 2015, from application No. PCT/US2015/040974.
Japanese Office Action dated Mar. 31, 2019, for Japanese Application No. 2018-094445.
Non-Final Office Action dated Dec. 4, 208, from U.S. Appl. No. 14/801,548.
Non-Final Office Action dated May 22, 2019, from U.S. Appl. No. 14/801,338.
Non-Final Office Action dated Nov. 20, 2018, from U.S. Appl. No. 14/801,266.
Non-Final Office Action dated Nov. 20, 2018, from U.S. Appl. No. 14/801,429.
Non-Final Office Action dated Oct. 10, 2019, from U.S. Appl. No. 14/801,266.
Non-Final Office Action dated Oct. 10, 2019, from U.S. Appl. No. 14/801,429.
Non-Final Office Action dated Oct. 29, 2019, from U.S. Appl. No. 14/801,548.
Notice of Allowance dated Aug. 16, 2018, from U.S. Appl. No. 15/896,954.
Notice of Allowance dated Aug. 16, 2018, from U.S. Appl. No. 15/897,048.
Notice of Allowance dated Aug. 30, 2019, from U.S. Appl. No. 14/801,338.
Notice of Allowance dated Aug. 8, 2018, from U.S. Appl. No. 15/896,904.
Notice of Allowance dated Mar. 20, 2019, from U.S. Appl. No. 16/184,839.
Notice of Allowance dated Mar. 29, 2019, from U.S. Appl. No. 16/184,854.
Russian Office Action dated Nov. 6, 2019, from application No. 2019112138.
U.S. Non-Final Office Action dated Jan. 22, 2019, from U.S. Appl. No. 16/184,839.
U.S. Non-Final Office Action dated Jan. 22, 2019, from U.S. Appl. No. 16/184,854.
U.S. Notice of Allowance dated Apr. 27, 2017, from related U.S. Appl. No. 15/344,442.
U.S. Notice of Allowance dated Aug. 5, 2016, from U.S. Appl. No. 14/803,880.
U.S. Notice or Allowance dated Aug. 5, 2016, from U.S. Appl. No. 14/803,944.
U.S. Notice of Allowance dated Jul. 29, 2016, from U.S. Appl. No. 14/801,503.
U.S. Notice of Allowance dated May 1, 2017, from related U.S. Appl. No. 15/344,453.
U.S. Notice of Allowance dated May 3, 2017, from related U.S. Appl. No. 15/344,449.
U.S. Notice of Allowance dated Nov. 6, 2017, from U.S. Appl. No. 15/655,815.
U.S. Notice of Allowance dated Nov. 7, 2017, from U.S. Appl. No. 15/655,839.
U.S. Notice of Allowance dated Nov. 8, 2017, from U.S. Appl. No. 15/655,826.
U.S. Office Action dated Apr. 18, 2016, from U.S. Appl. No. 14/801,503.
U.S. Office Action dated Apr. 19, 2016, from U.S. Appl. No. 14/803,944.
U.S. Office Action dated Apr. 19, 2018, from U.S. Appl. No. 14/801,338.
U.S. Office Action dated Apr. 20, 2016, from U.S. Appl. No. 14/803,880.
U.S. Office Action dated Apr. 20, 2018, from U.S. Appl. No. 15/896,954.
U.S. Office Action dated Apr. 20, 2018, from U.S. Appl. No. 15/897,048.
U.S. Office Action dated Apr. 6, 2018, from U.S. Appl. No. 15/896,904.
U.S. Office Action dated Aug. 25, 2017, from U.S. Appl. No. 15/655,826.
U.S. Office Action dated Jan. 20, 2017, from related U.S. Appl. No. 15/344,442.
U.S. Office Action dated Jan. 20, 2017, from related U.S. Appl. No. 15/344,449.
U.S. Office Action dated Jan. 20, 2017, from related U.S. Appl. No. 15/344,453.
U.S. Office Action dated Jan. 24, 2018, from U.S. Appl. No. 14/801,548.
U.S. Office Action dated Jan. 25, 2018, from U.S. Appl. No. 14/801,429.
U.S. Office Action dated Jan. 29, 2018, from U.S. Appl. No. 14/801,266.
U.S. Office Action dated Sep. 11, 2017, from U.S. Appl. No. 15/655,839.
U.S. Office Action dated Sep. 7, 2017, from U.S. Appl. No. 15/655,815.
Israeli Office Action dated Apr. 5, 2020, from application No. 249567.
Non-Final Office Action dated Jun. 19, 2020, from U.S. Appl. No. 14/801,266.
Notice of Allowance dated May 29, 2020, from U.S. Appl. No. 14/801,548.
Non-Final Office Action dated Jul. 27, 2020, from U.S. Appl. No. 14/801,429.
Australian Examination Report dated Feb. 1, 2021, from application No. 2020203469.
Final Office Action dated Feb. 4, 2021, from U.S. Appl. No. 14/801,266.
Korean Office Action dated Jan. 27, 2021, from application No. 10-2020-7037331.
Notice of Allowance dated Apr. 30, 2021, from U.S. Appl. No. 14/801,429.

(56) References Cited

OTHER PUBLICATIONS

Notice of Allowance dated Jul. 26, 2021, from U.S. Appl. No. 14/801,266.

\* cited by examiner

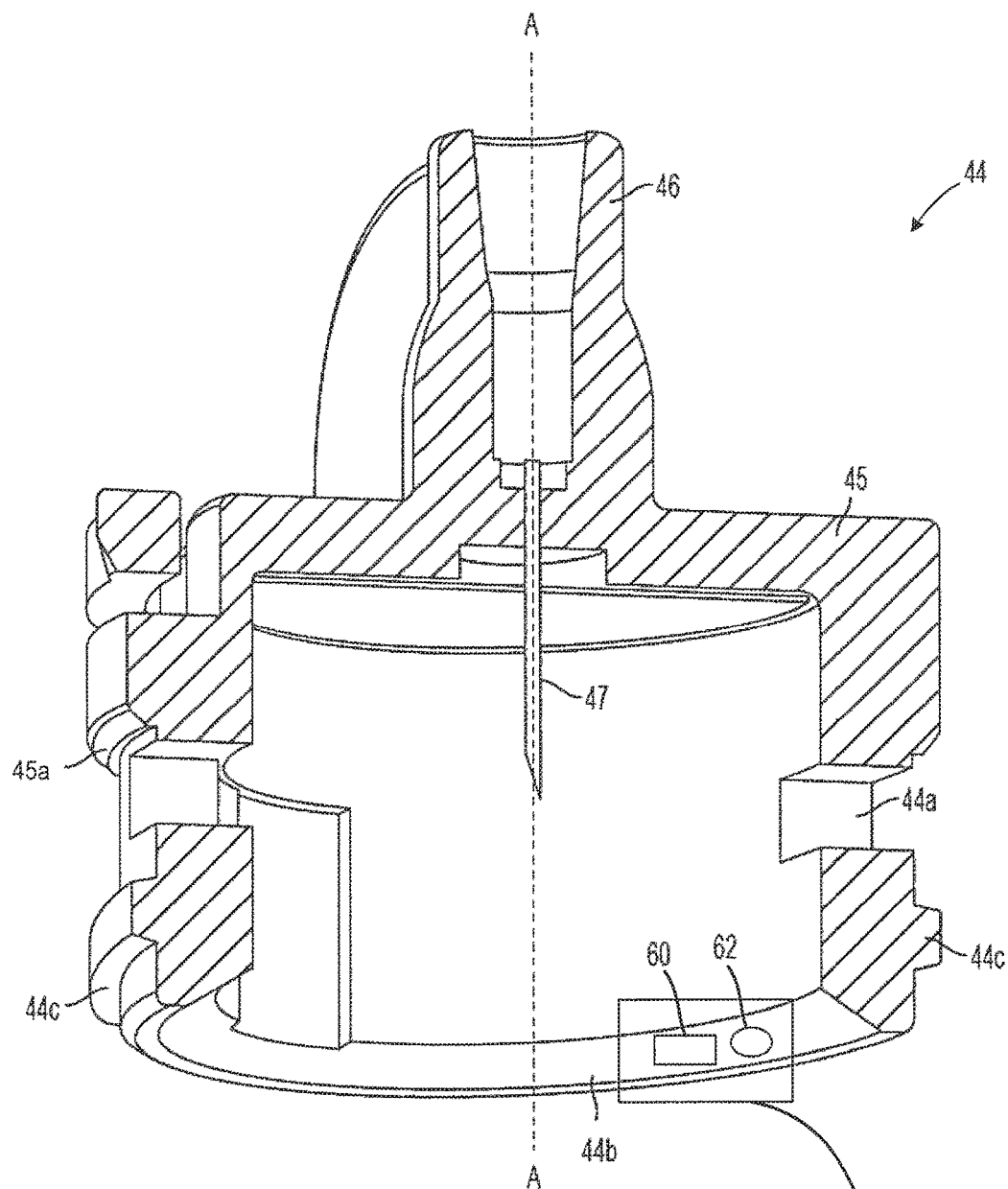
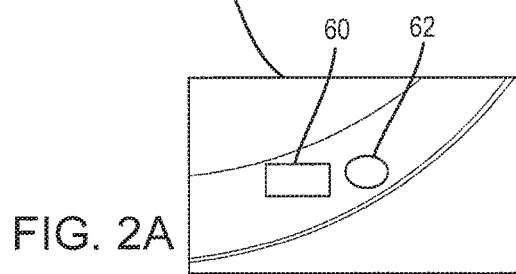
FIG. 2
FIG. 2A

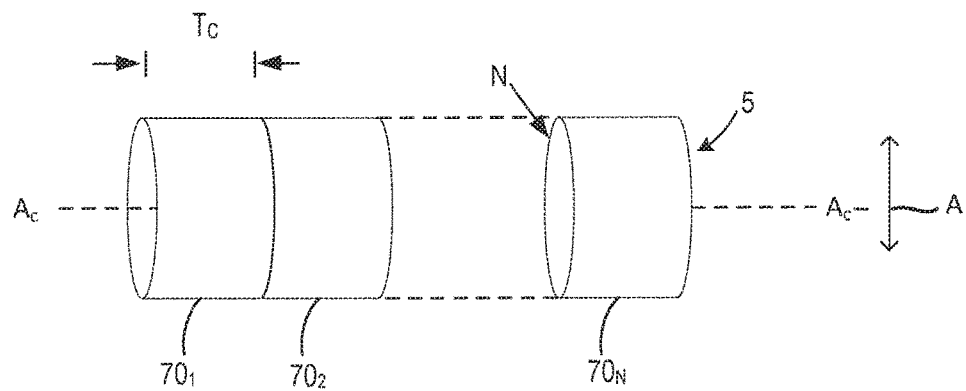
FIG. 8
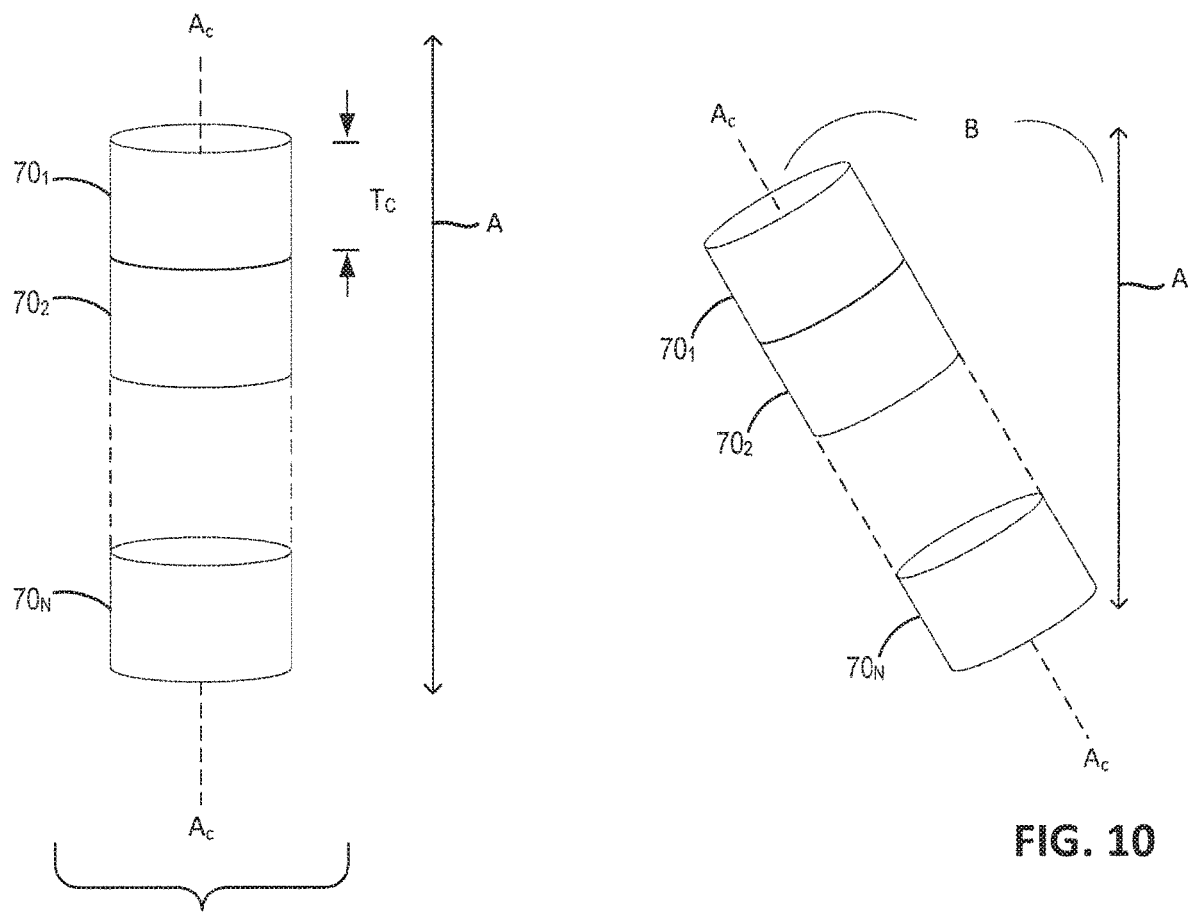
FIG. 9
FIG. 10

RESERVOIR CONNECTION INTERFACE WITH DETECTABLE SIGNATURE

BACKGROUND OF THE INVENTION

1. Field of the Invention

The present disclosure relates to connection interfaces for syringes and reservoirs and, in particular embodiments, to connection interfaces for interfacing a syringe or reservoir to an infusion pump, infusion set tubing, or both, and for providing any one of a plurality of different detectable signatures or detectable signals in an efficient manner. Further embodiments relate to infusion pump systems and infusion set systems that include such connection interfaces, and to methods that employ the same.

2. Description of the Related Art

Infusion pump devices and systems are used in medical contexts, to deliver or dispense infusion media to patients, where such infusion media may be, for example, a prescribed medication such as insulin, a cancer therapy drug, an HIV therapy drug or other media for treating a medical or biological condition. In one form, such infusion pump devices have a relatively compact pump housing adapted to receive a syringe or reservoir that contains a prescribed medication for administration to a patient.

Infusion pump devices typically include a small drive motor connected through a drive linkage to a piston in the syringe or reservoir. The drive motor operates to selectively move the piston within the syringe or reservoir, to drive fluidic media from the reservoir and to the user. Programmable controls are normally provided for operating the drive motor continuously or at periodic intervals to obtain a controlled delivery of the medication over a period of time. Such infusion pumps are utilized to administer insulin and other medications, with exemplary pump constructions being shown and described in U.S. Pat. Nos. 4,562,751; 4,678,408; 4,685,903; 5,080,653 and 5,097,122, each of which is incorporated by reference herein, in its entirety.

Infusion sets are tubing and connection apparatus that provide a fluid flow path for infusion media to flow from the reservoir or syringe in the pump to the user. Connectors for attaching the infusion set tubing to the reservoirs can take various forms. Some examples of such connectors are described in U.S. Pat. No. 6,585,695, which is incorporated by reference herein, in its entirety.

SUMMARY

Connection interfaces for syringes and reservoirs are configured for interfacing a syringe or reservoir to an infusion pump, infusion set tubing, or both. Infusion pump systems include infusion pump devices, infusion sets and connection interfaces that connect the infusion pump devices with the infusion sets. In particular embodiments, a connection interface includes a cap configured to be secured to a reservoir to form a reservoir/cap unit (or base/reservoir/cap unit) that is configured to be installed within a reservoir receptacle of an infusion pump device. Further embodiments relate to infusion pump systems that include that connection interface, as well as an infusion pump device and a reservoir.

In particular embodiments, at least one detectable feature is arranged on the cap for detection by at least one sensor element when the reservoir of the reservoir/cap unit is received in the reservoir receptacle of the infusion pump device. The sensor element may be any one or more of a magnetic detection sensor or an inductive sensor. Similarly, the detectable feature may be any one or more of a magnetically detectable feature or one or more inductively detectable feature.

According to an example embodiment, a connector interface system includes a cap to connect to a reservoir to form a reservoir/cap unit for installation into an infusion pump device. The cap has at least one receptacle for receiving one or more detectable features. At least one detectable feature comprising at least one disc-shaped member is received within the at least one receptacle, for detection by at least one sensor element on the infusion pump device when the reservoir of the reservoir/cap unit is received in a reservoir receptacle of the infusion pump device. The at least one detectable feature has at least one detectable parameter that is associated with one or more characteristics of the cap, the reservoir, the infusion pump device, a cannula associated with the cap or a tubing connected between the cap and the cannula.

In a further example of a connector interface system as described above, the at least one detectable feature includes a plurality of disc-shaped members arranged in a stack within the at least one receptacle.

In a further example of a connector interface system as described above, the at least one receptacle includes a plurality of receptacles, each receptacle configured for receiving one or more detectable features.

In a further example of a connector interface system as described above, the at least one detectable feature includes a plurality of disc-shaped members arranged in a stack within one of the at least one receptacle, while the other of the at least one receptacles is devoid of disc-shaped members.

In a further example of a connector interface system as described above, the at least one detectable feature includes a plurality of disc-shaped members arranged in a stack within each of the plurality of receptacles.

In a further example of a connector interface system as described above, the cap and the reservoir have a common longitudinal axis A, and wherein the at least one receptacle includes a first receptacle having a partial cylindrical or semi-cylindrical configuration, having a cylindrical axis that extends in a direction transverse to the direction of the axis A.

In a further example of a connector interface system as described above, the at least one receptacle includes a second receptacle having a cylindrical configuration with a cylindrical axis that extends in a direction parallel to the direction of the axis A.

In a further example of a connector interface system as described above, the at least one receptacle includes a second receptacle having a cylindrical configuration with a cylindrical axis that extends in a direction that is at an oblique angle relative to the direction of the axis A.

In a further example of a connector interface system as described above, the cap and the reservoir have a common longitudinal axis A, and wherein the at least one receptacle includes a receptacle having a cylindrical configuration with a cylindrical axis that extends in a direction parallel to the direction of the axis A.

In a further example of a connector interface system as described above, the cap and the reservoir have a common longitudinal axis A, and wherein the at least one receptacle includes a plurality of receptacles including a first receptacle having a cylindrical configuration with a cylindrical axis that extends in a direction that is at an oblique angle relative to the direction of the axis A.

In a further example of a connector interface system as described above, the at least one disc-shaped member includes at least one disc-shaped magnet, and wherein the at least one detectable feature provides a detectable magnetic field.

In a further example of a connector interface system as described above, the cap and the reservoir have a common longitudinal axis A, and wherein the at least one detectable parameter includes at least one of a magnitude of the magnetic field, a polarity direction of the magnetic field and an angle of the magnetic field relative to the axis A.

In a further example of a connector interface system as described above, the at least one disc-shaped member includes a plurality of disc-shaped magnets, and wherein the detectable magnetic field is dependent on the number of disc-shaped magnets in the detectable feature, and wherein the number of disc-shaped magnets in the detectable feature is adjustable.

In a further example of a connector interface system as described above, the at least one disc-shaped member includes at least one disc-shaped electrically conductive member, and wherein the at least one detectable feature provides an inductively detectable signature.

In a further example of a connector interface system as described above, the at least one disc-shaped member includes a number of disc-shaped electrically conductive member, the number being greater than one, and wherein the inductively detectable signature is dependent on the number of disc-shaped members in the detectable feature, and wherein the number of disc-shaped members in the detectable feature is adjustable.

A connector interface system according to a further embodiment includes a cap to connect to a reservoir to form a reservoir/cap unit for installation into an infusion pump device. The cap has at least one receptacle for receiving one or more detectable features. At least one detectable feature is received within the at least one receptacle. The at least one detectable feature includes a number of detectable members, the number being greater than one, wherein each detectable member has the same shape and size and configured to be selectively received within the at least one receptacle, for detection by at least one sensor element on the infusion pump device when the reservoir of the reservoir/cap unit is received in a reservoir receptacle of the infusion pump device. The at least one detectable feature has at least one detectable parameter that is dependent, at least in part, on the number of detectable members received within the at least one receptacle. The at least one detectable parameter is associated with one or more characteristics of the cap, the reservoir, the infusion pump device, a cannula associated with the cap or a tubing connected between the cap and the cannula.

In a further example of a connector interface system as described above, the at least one detectable feature includes at least one disc-shaped magnet that provides a detectable magnetic field.

In a further example of a connector interface system as described above, the at least one detectable feature includes at least one disc-shaped electrically conductive member, and wherein the at least one detectable feature provides an inductively detectable signature.

In a further example of a connector interface system as described above, the one or more characteristics includes one or more of: a type or identity of a manufacturer of the reservoir, or the cap; a size of the reservoir or the cap; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir or the cap; a location corresponding to a place where the reservoir or infusion media in the reservoir was made, filled, or otherwise processed; a location corresponding to a place where the cap was made, assembled or otherwise processed; a location corresponding to a place where the reservoir, infusion media in the reservoir or the cap is authorized to be used; a lot number or code associated with a batch in which the reservoir, the cap or infusion media was made, cleaned, filled or otherwise processed; a serial number; a unique ID; user identification information for authorized users; a type, length or size of a cannula associated with the cap; or a type, length or size of a tubing connected between the cap and the cannula.

A method of using a connector interface system according to an embodiment includes connecting a cap to a reservoir to form a reservoir/cap unit for installation into an infusion pump device, where the cap has at least one receptacle for receiving one or more detectable features. The method further includes inserting at least one detectable feature including a number of disc-shaped members within the at least one receptacle, for detection by at least one sensor element on the infusion pump device when the reservoir of the reservoir/cap unit is received in a reservoir receptacle of the infusion pump device, the number of disc-shaped members being greater than one. The at least one detectable feature has at least one detectable parameter that is dependent, in part, on the number of disc-shaped members. The at least one detectable parameter is associated with one or more characteristics of the cap, the reservoir, the infusion pump device, a cannula associated with the cap or a tubing connected between the cap and the cannula. The at least one detectable parameter includes a magnet field signature or an inductively detectable signature.

BRIEF DESCRIPTION OF THE DRAWINGS

FIG. 2 is an enlarged, side, cross-section view of a cap of a reservoir connection interface apparatus.

FIG. 2A is an enlarged section view of a portion of the cap in FIG. 2.

FIG. 8 is a perspective view of a detectable feature in a first orientation.

FIG. 9 is a perspective view of a detectable feature in a second orientation.

FIG. 10 is a perspective view of a detectable feature in a third orientation.

DETAILED DESCRIPTION

In the following description, reference is made to the accompanying drawings which form a part of this application and which illustrate several embodiments of the present invention. It is understood that other embodiments may be utilized and structural and operational changes may be made without departing from the scope of the present invention.

In various drawings, like numerals are used to represent the same elements or similar elements that may perform or operate in a similar manner. The use of the term "and/or" herein is intended to represent an "inclusive OR." In addition, the user of the term "or" herein is intended to represent an "inclusive OR" except where such a meaning would not make sense.

Embodiments of the present invention relate to connection interfaces for syringes and reservoirs. Particular embodiments relate to connection interfaces for interfacing a syringe or reservoir to an infusion pump device, an infusion set tubing, or both. Further embodiments relate to infusion pump systems and infusion set systems that include such connection interfaces, and to methods of making and using such connection interfaces and systems. One or more aspects of present invention may be employed or included in connection interfaces, infusion pump systems and infusion set systems of the type described in U.S. Pat. Nos. 6,585,695 and 9,452,255 (each of which is incorporated by reference herein, in its entirety), or in other suitable connection interfaces, infusion pump systems and infusion set systems.

Figure 1:
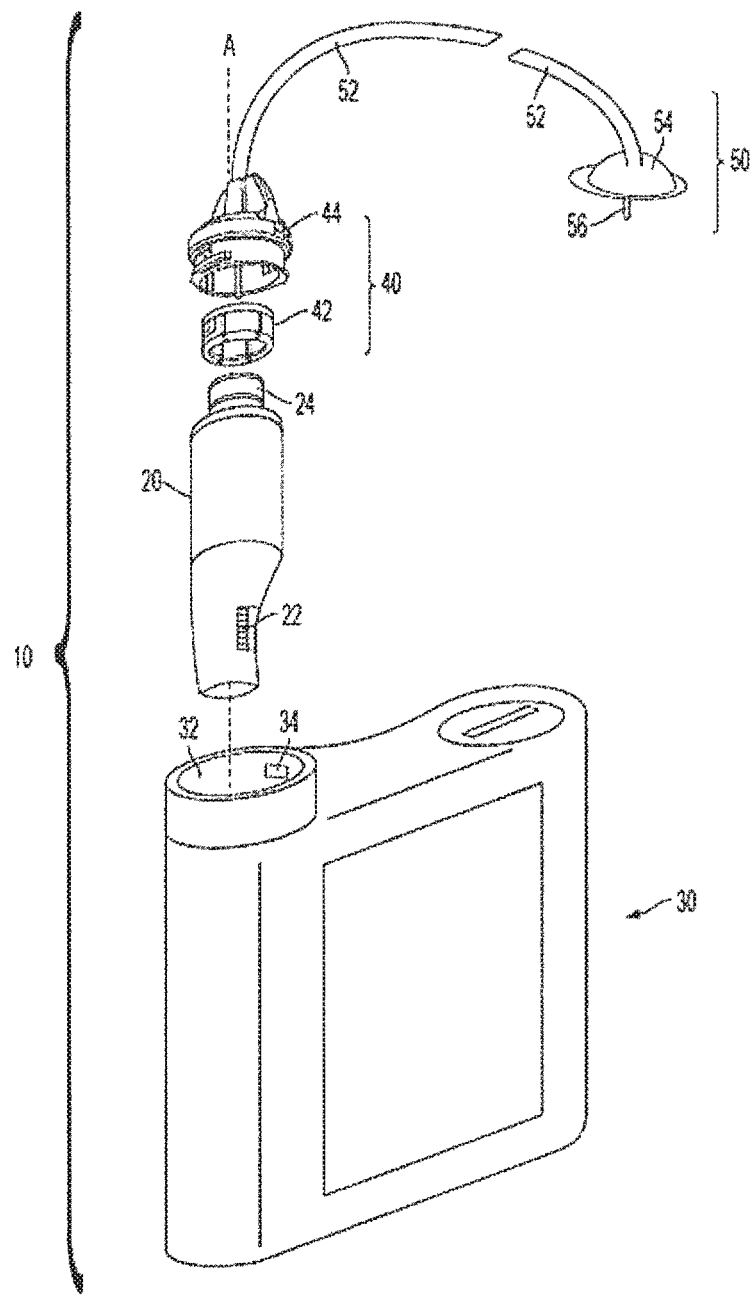
FIG. 1 is a partially exploded, perspective view of an infusion pump system including an infusion pump device, a reservoir, an infusion set, and a connection interface apparatus.

An infusion pump system 10 according to an example embodiment of the present invention is shown, in a partially exploded, perspective view, in FIG. 1. The infusion pump system 10 in FIG. 1 includes a reservoir 20, an infusion pump device 30, a connection interface 40, and an infusion set 50. Further system embodiments may include one or more, but not all of the above-noted components, and/or additional components not shown in FIG. 1.

The reservoir 20 is an enclosed container that has an interior volume containing an infusion media. The infusion media may be, for example, a prescribed medication such as insulin, a cancer therapy drug, an HIV therapy drug or other media for treating a medical or biological condition. As described below, the reservoir 20 is configured to be received within a receptacle 32 of the infusion pump device 30 and to interface with a drive device (not shown) located within the infusion pump device, for selectively driving infusion media from the reservoir in a controlled manner. The reservoir 20 is also configured to be connected in fluid flow communication with the infusion set 50, for providing a flow path for infusion media from the reservoir to a user. In particular embodiments described herein, the connection interface 40 is configured to connect and interface the reservoir 20 with the infusion set 50 and with the infusion pump device 30, using releasable coupling structure.

The infusion set 50 includes a tubing 52 and a needle or cannula housing 54. In particular embodiments, the tubing 52 may be generally flexible and bendable. The needle or cannula housing 54 is configured to be secured to a user, such as, but not limited to, adhering the housing 54 to a user's skin, at a desired infusion location on the user. The housing 54 may include adhesive material on its base, or other suitable material or structure, for securing the housing 54 to the user's skin. The housing 54 contains and supports a hollow needle or cannula 56 that is in fluid flow communication with the tubing 52 and that is configured to extend (or to be extended) out from the base and into the user's skin, when the housing 54 is secured to the user's skin. When extended into a user's skin, the hollow needle or cannula 56 can convey infusion media from the tubing 52, into the user. Examples of infusion sets that may be employed as an infusion set 50 include, but are not limited to a Quickset® infusion set, a Silhouette® infusion set, a SureT® infusion set, a Mio® infusion set, or the like. However, other embodiments of the present invention may include or operate with other suitable infusion set configurations.

100461 Examples of infusion pump devices that may be employed as an infusion pump device 30 include, but are not limited to a Paradigm® infusion pump, a Revel™ infusion pump, a MiniMed® 530 G infusion pump, MiniMed 640 G, or the like. Other examples include those described in U.S. Pat. Nos. 4,562,751; 4,678,408; 4,685,903; 5,080,653 and 5,097,122, each of which is incorporated by reference herein, in its entirety. However, other embodiments of the present invention may include or operate with other suitable infusion pump devices. The infusion pump device 30 includes a drive motor or other drive device with drive linkage (not shown) arranged to engage corresponding drive linkage 22 on a piston in the reservoir 20, when the reservoir 20 is properly received within the reservoir receptacle 32. In particular embodiments, the drive linkage 22 corresponds to an "engagement side 128" described in U.S. Pat. No. 8,167,846 titled "Reservoir Filling Systems And Methods", which is incorporated herein by reference, in its entirety. In other embodiments, other suitable drive linkage structure is employed as the drive linkage 22 for operatively coupling the piston in the reservoir 20 to the drive device in the infusion pump device 30, when the reservoir 20 is received in the reservoir receptacle 32 of the infusion pump device 30.

The drive device operates to selectively move the piston within the syringe or reservoir, to drive fluidic media from the reservoir and to the user. The infusion pump device 30 includes control electronics connected to the drive device for controlling the drive device to selectively drive the piston and dispense fluid from the reservoir and into the tubing 52 of the infusion set 50. In particular embodiments, the control electronics are programmable to deliver fluid from the reservoir continuously or at one or more predefined intervals over time, in accordance with one or more programmed delivery routines. The control electronics may be further configured to operate one or more display devices and user input devices on or associated with the infusion pump device. The control electronics may be included in or be connected with the electronics 80 described below with reference to FIG. 11.

In the embodiment of FIG. 1, the connection interface 40 includes a base 42 and a connection cap 44. In other embodiments, the base 42 is omitted or is formed as part of (unitary with or fixed to) the reservoir 20 or the cap 44. In the embodiment of FIG. 1, the base 42 is a separate element that is fixedly attached to the reservoir 20 by securing it around a swage 24 of the reservoir 20, during (or after) manufacturing of the reservoir 20. For example, the base 42 may include one or more slots 42a and may be made of a rigid, but sufficiently malleable material that can be crimped over the swage 24 to secure the base 42 to the reservoir 20. In particular embodiments, the base 42 is fixedly connected to the reservoir 20 in a manner that inhibits rotation or motion of the base 42 relative to the reservoir 20. Other embodiments may include other suitable structure or materials for securing the base 42 to the swage 24. In other embodiments of the present invention, the base 42 is configured to be attachable to (and removable from) the reservoir, so that the connector interface could be used with reservoirs, cartridges or syringes that were not initially manufactured on the base.

The base 42, swage 23 and the cap 44 may be made of any one or more suitable materials having sufficient rigidity and strength to operate as described herein, including, but not limited to plastic, metal, ceramic, composite or other suitable material. In particular embodiments, the cap 44 is made of a molded plastic material.

Figure 3:
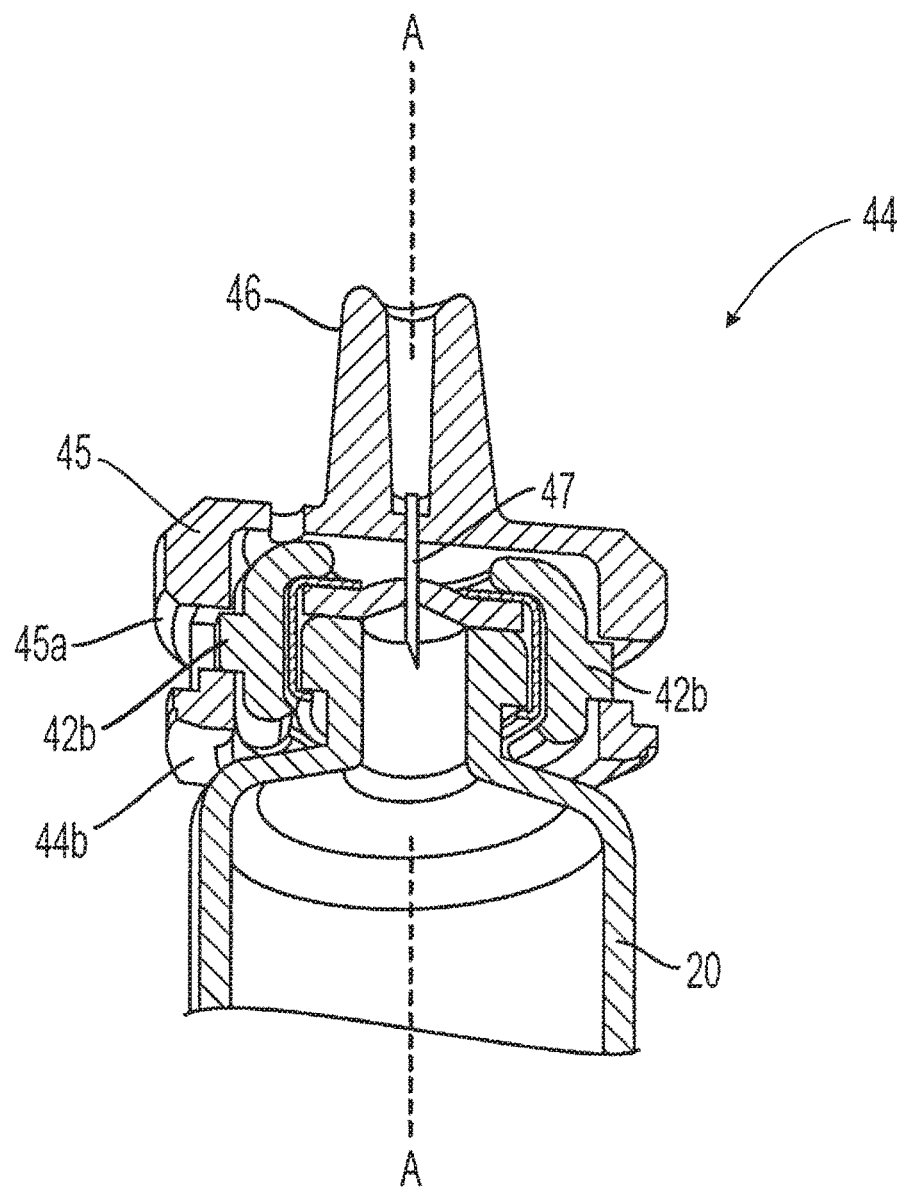
FIG. 3 is a partial side, cross-section view of the cap of the embodiment of FIG. 2, connected with a reservoir.
Figure 4:
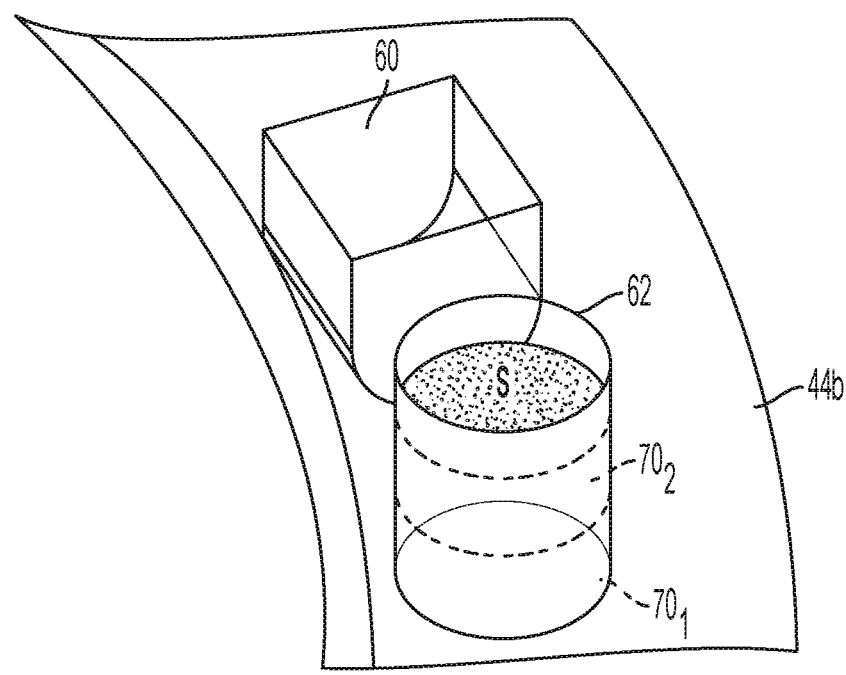
FIG. 4 is a partial bottom, perspective view of the cap of the embodiment of FIG. 2, including a detectable feature in a first configuration.

The cap 44 of the connector interface 40 connects, in fluid flow communication, with the tubing 52 of the infusion set 50. An example embodiment of the cap 44 is shown in FIGS. 2 and 3. A cross-section view of the cap 44 is shown in FIG. 2, with the cap separated from a reservoir. A cross-section view of the cap 44 is shown in FIG. 3, with the cap attached to a neck portion of a reservoir 20. In the embodiment of FIGS. 2 and 3, the cap 44 includes a body 45 forming a housing having an open end that opens into an interior volume of the cap housing. The cap 44 also includes a tubing port 46 that connects with the tubing 52 of the infusion set 50 in any suitable manner, including, but not limited to a friction fit, clamp, adhesive, combinations thereof, or the like. In particular embodiments, the cap 44 is connected with the tubing 52 during manufacture or assembly of the cap 44, before the cap 44 is made available to the user. In other embodiments, the cap 44 has a port configured to be connected to the tubing 52 after manufacture of the cap, for example, by the user, medical technician or other authorized person. The cap 44 also includes a hollow needle 47 located internal to the cap housing and provided in fluid flow communication with the tubing port 46. In particular embodiments, the cap 44 may correspond to a cap 4 as described in the above-cited U.S. Pat. Nos. 6,585,695 and 9,452,255. In other embodiments, the cap 44 may have another suitable configuration.

The cap 44 is removably attached or attachable to the base 42 (and, thus, to the reservoir 20) with a first releasable coupler. In embodiments in which the base 42 is omitted, the first releasable coupler removably attaches the cap 44 directly to the reservoir 20. In addition, the cap 44 is removably attached or attachable to the infusion pump device 30 with a second releasable coupler. In particular embodiments, the first releasable coupler includes any suitable structure that allows selective coupling and decoupling of the cap with the base 42, while the second releasable coupler includes a similar or different structure that allows selective coupling and decoupling of the cap 44 with the infusion pump device 30. Example embodiments of first releasable couplers for coupling a cap to a base of a connection interface, and second releasable coupler for coupling a cap to an infusion pump device are described in the above-cited U.S. Pat. No. 6,585,695.

In one embodiment, the first releasable coupler includes one or more protrusions (extending features) or receptacles (openings, slots or detents) provided on one of the base 42 or the cap 44, and corresponding receptacle or protrusion in the other of the base 42 or the cap 44, for receiving the protrusions. An example embodiment of a first releasable coupler is described with reference to the cap 44, base 42 and reservoir 20 shown in FIGS. 2 and 3, wherein protrusions 42b on the base 42 are received within slots or openings 44a in the cap 44. In other embodiments, other suitable coupler structures for releasably coupling or permanently coupling the cap 44, base 42 and reservoir 20 (or for releasably coupling or permanently coupling the cap 44 directly to the reservoir 20) are employed.

Accordingly, in particular examples, the base 42 is connected to the reservoir 20, to form an integrated unit with the reservoir 20. The integrated unit of the reservoir 20 and the base 42 is, in turn, connected to the cap 44. For example, in the embodiment of FIG. 1, the integrated base/reservoir unit is connected to the cap 44 by inserting the base 42 into an open, lower end of the cap 44, and engaging the protrusions and receptacles on the base 42 and the cap 44. Thus, the base/reservoir unit may be connected with the cap 44 to form an integrated base/reservoir/cap unit. (In embodiments in which the base 42 is omitted or incorporated in the reservoir or cap, the references made herein to a base/reservoir/cap unit shall be read to mean reservoir/cap unit.) When the cap 44 is coupled to the reservoir 20 (as shown in FIG. 3), a surface 44b of the cap 44 (i.e., the downward facing surface of the cap 44 in the orientation shown in FIGS. 2 and 3) faces the reservoir 20.

In particular embodiments, the internal needle 47 of the cap 44 is disposed so that when the base/reservoir unit is fully inserted in the cap 44, the needle pierces a septum (not shown) of the reservoir 20. In such embodiments, the insertion motion and force of the base/reservoir unit into the open end of the cap 44, to connect the base/reservoir unit to the cap 44, causes the needle 47 to pierce the reservoir septum, permitting fluid in the reservoir to flow into the needle 47 and the tubing 52 of the infusion set 50. In certain embodiments, the base 42 (after connection with the cap 44) may be selectively disconnected from the cap 44, by manually moving the cap 44 relative to the base 42 in an opposite directed motion relative to the direction of motion for connection, to move the protrusions 42b out of the receptacles 44a.

As shown in FIG. 1, the cap 44 connects to the base 42 and the reservoir 20 along a common axis A, to form a unit (a base/reservoir/cap unit). When connected together, the base/reservoir/cap unit may be received within a reservoir receptacle 32 of an infusion pump device 30, along the axis A. The axis A in FIG. 1 corresponds to the longitudinal axis of the reservoir 20 and of the reservoir receptacle 32, and the direction of insertion as the base/reservoir/cap unit is inserted (or aligned to be inserted) into the reservoir receptacle 32. The axis A also corresponds to the central axis of the cap 44 and base 20 in FIG. 1. When the base/reservoir/cap unit is received within a reservoir receptacle 32, a surface 45a of the cap body 45 may abut or seal against a surface of the infusion pump device, around the reservoir receptacle 32.

When properly installed within the reservoir receptacle 32, the cap 44 (or base/reservoir/cap unit) is releasably secured in the housing of an infusion pump device 30, for example, with the second releasable coupler. In the embodiment of FIGS. 1 and 2, the second releasable coupler includes external threads 44c on the housing 45 of the cap 44. The threads 44c are arranged to engage corresponding threads (not shown) in a reservoir receptacle 32 of the infusion pump device 30 in order to secure the base/reservoir/cap unit to the infusion pump device 30. In other embodiments, the second releasable coupler includes other suitable coupling structures for coupling the cap 44 to the infusion pump device 30 in a selectively releasable manner, including but not limited to structures as described in the above-cited U.S. Pat. No. 6,585,695.

Accordingly, the cap 44 may be configured as described above, for selectively coupling the reservoir 20 to an infusion set 50, and for securing the base/reservoir/cap unit to the infusion pump. In certain examples, the cap 44 may be manufactured and configured (by being molded, machined, or formed by other suitable manufacturing techniques), to couple to and operate with one particular type, model or version of an infusion pump 30. In other examples, the cap 44 may be manufactured to couple to and operate with any one of a plurality of different types, models, or versions of infusion pumps.

Some types, models or versions of infusion pumps (such as, but not limited to those described in the above-cited U.S. Pat. No. 9,452,255) may include sensing features for sensing or detecting information regarding the cap 44. Accordingly, in some examples, the cap 44 is configured with one or more detectable features, such that the cap 44 may be coupled to and operate with one or more types, models or versions of infusion pumps that include sensing features, for sensing or detecting information regarding the cap 44. However, other types, models or versions of infusion pumps may not include or operate with such sensing features. Accordingly, in some examples, the cap 44 is configured such that the cap may be readily manufactured without the one or more detectable features (for operation with infusion pumps that do not have or operate with sensing features), or by making relatively minor or minimal adjustments to manufacturing processes, the cap may be readily manufactured with the one or more detectable features (for operation with infusion pumps having sensing features). In particular examples, the one or more detectable features may have any one of a plurality of different configurations, each providing a different detectable signal or signature. In particular examples, the cap 44 is made with a manufacturing process that efficiently allows multiple separate caps to be made, where each cap (or a group of caps) has a different detectable feature configurations relative to each other cap (or relative to the caps in each other group of caps).

In certain examples, the cap 44 is formed with and includes one or more (or a plurality of) receptacles for receiving and holding one or more (or a plurality of) detectable features. The one or more (or plurality of) detectable features may be inserted and received within the one or more (or plurality of) receptacles. In certain examples, the cap 44 may be formed either with or without the one or more (or plurality of) receptacles for holding detectable features, by selectively making a relatively minor adjustment to a molding process (or other manufacturing process), during manufacturing or post-manufacturing of the cap 44.

For example, in certain embodiments, a molding process is used to form the cap 44 (or portions of the cap 44), where a mold is configured to define the cap body 45 (or portions of the cap body 45) including the surface 44b. The mold includes a section having a relief shape for forming the surface 44b, where that mold section includes one or more mounting structures (such as, but not limited to openings, brackets or other receptacles) that are configured to selectively receive either pins or plugs. When manufacturing a cap 44 to have one or more receptacles for holding detectable features, that mold section is prepared (by a technician, automated system or the like) by adding the pins to the mounting structures. On the other hand, when manufacturing a cap 44 to be devoid of receptacles for holding detectable features, that same mold section is prepared (by a technician, automated system or the like) by adding the plugs (instead of pins) to cover the mounting structures.

In such examples, the pins include a head that extends partially into the relief shape and has a head shape corresponding to the shape of one or more receptacles (such as, but not limited to, the receptacles 60 and 62 described below). Accordingly, when the pins are mounted to the mold section and the cap 44 is molded, the pins form (during the molding process) one or more recesses within the surface 44b, corresponding to the shape of one or more receptacles. On the other hand, the plugs include a generally flat or planar surface that result in a surface 44b devoid of receptacles. Accordingly, when the plugs are mounted to the mold section (instead of the pins) and the cap is molded, the cap can be made to be devoid of the receptacles for holding detectable features. Therefore, in certain examples, a relatively simple adjustment in the manufacturing process (to either mount pins or to mount plugs to the mold section) can be made to determine whether a cap 44 has one or more receptacles for holding detectable features or does not having such receptacles.

In the example in FIGS. 2 and 2A, the cap 44 has two receptacles 60 and 62, each receptacle having an interior volume of a shape and size for receiving and holding one or more detectable features. Other examples may include more than two receptacles, or a single receptacle. In FIGS. 4-7, the receptacles 60 and 62 are shown as containing or holding detectable features in various different arrangements.

In the example in FIGS. 2-7, the receptacles 60 and 62 are located on the surface 44c of the cap 44 that faces the reservoir 20, when the cap 44 is coupled to the reservoir 20 (i.e., the downward facing surface of the cap 44 in the orientation shown in FIGS. 2 and 3). In particular examples, that surface 44c is located within the reservoir receptacle 32 of the infusion pump device 30, when the base/reservoir/cap unit is fully received by the reservoir receptacle 32 and coupled to the infusion pump device 30. Accordingly, the surface 44c can be located adjacent one or more sensor element(s) 34 in the infusion pump device 30, when (or only when) the base/reservoir/cap unit is fully received by the reservoir receptacle 32 and coupled to the infusion pump device 30. The surface 44c extends circumferentially around the axis A of the cap and, thus, can provide multiple suitable locations on which the one or more receptacles (such as receptacles 60 and 62), may be located for sufficient alignment with any one or more of multiple locations on the infusion pump device 30 at which one or more sensor element(s) 34 may be provided. In certain examples in which the cap 44 is formed by molding processes, the surface 44c can be readily configured to include one or more (or a plurality of) receptacles (such as receptacles 60 and 62) at one or more suitable locations along the surface 44c, by relatively simple adjustments to a mold (or mold section) in which the cap 44 is formed, as described herein. However, in other examples, the receptacles 60 and 62 may be located on other suitable surfaces or locations of the cap 44 (such as, but not limited to, other suitable locations below the abutment or seal surface 45a of the cap body 45, in the orientation of FIGS. 2 and 3). Also, in other examples, the receptacles 60 and 62 may be formed by any suitable manufacturing or post-manufacturing processes.

In the example in FIGS. 2-7, the receptacles 60 and 62 are each configured to receive and hold one or more disc-shaped members, where the one or more disc-shaped members define a detectable feature. In particular examples, each disc-shaped member is a disc-shaped magnet. Such disc-shaped magnets may include any suitable permanent magnet material. In further embodiments, the disc-shaped magnets include, but are not limited to, magnetically conductive materials connected with permanent or electromagnets magnets, electromagnets, or other suitable magnetized material or device.

For example, each disc-shaped member may have relatively small dimensions, such as a diameter of about 1 mm. and a thickness of about 1 mm. In other examples, such disc-shaped magnets may have other suitable dimensions (including, but not limited to a diameter within the range of about 0.5 mm. to about 4 mm. and a thickness of up to about 10 mm.). In particular examples, such disc-shaped magnets can be readily available and relatively inexpensive disc-shaped members (such as, but not limited to, multi-purpose disc-shaped magnets or metal discs that are readily available in the marketplace or that can be efficiently manufactured). Accordingly, the use of relatively small, disc-shaped magnets can decrease the cost of the detectable features and the cap 44.

A single disc-shaped magnet, alone, can provide a limited amount of variable detectable information. However, multiple disc-shaped magnets can be arranged to provide a greater number of detectable signal variations, depending upon the location and arrangement of the magnets. Accordingly, embodiments described herein include one or more receptacles (such as, but not limited to the receptacles 60 and 62) that are configured to receive and hold multiple disc-shaped magnets, in various different orientations, locations, or combinations thereof, for providing various different detectable signals depending upon the orientation and location of the magnets. In addition, embodiments described herein may be configured to provide such various different magnet orientations and magnet locations, while also reducing or minimizing the manufacturing complexity and costs to accommodate such different variations.

As shown in FIGS. 8, 9 and 10, multiple disc-shaped magnets may be arranged in various stacked arrangements (where each stack has one or more disc-shaped magnets), to provide various different detectable signals. In FIGS. 8, 9 and 10, each individual or single disc-shaped magnet has a cylindrical, disc shape defining a cylindrical axis $A_c$, a thickness dimension $T_c$ and a diameter dimension. Each disc-shaped magnet has opposing poles on opposite disc surfaces. For example, each disc-shaped magnet may have a north magnetic pole on the upward-facing surface in FIGS. 9 and 10 or the left-facing surface in FIG. 8, and a south magnetic pole on the downward-facing surface in FIGS. 9 and 10 or the right-facing surface in FIG. 8. Alternatively, each disc-shaped magnet may have a north magnetic pole on the downward-facing surface in FIGS. 9 and 10 or the right-facing surface in FIG. 8 and a south magnetic pole on the upward-facing surface in FIGS. 9 and 10 or the left-facing surface in FIG. 8. In other examples, the magnetic field direction of a (or each) disk-shaped magnet may be set (during manufacture or post-manufacturing processes) at a pre-determined and detectable oblique angle relative to the cylindrical axis $A_c$. Accordingly, each of the stacks of disc-shaped magnets in FIGS. 8-10 can selectively provide two (or more) different magnetic signals, depending upon the direction selected for the magnetic poles.

As shown in FIG. 8, any suitable number of disc-shaped magnets $70_1, 70_2, \ldots 70_N$ (where N represents any suitable whole number) may be arranged co-axially, in a stack, with their axes arranged in a direction perpendicular to the direction of the axis A of the cap 44. As shown in FIG. 9, any suitable number of disc-shaped magnets $70_1, 70_2, \ldots 70_N$ (where N represents any suitable whole number) may be arranged co-axially, in a stack, with their axes arranged in a direction parallel to the direction of the axis A of the cap 44. As shown in FIG. 10, any suitable number of disc-shaped magnets $70_1, 70_2, \ldots 70_N$ (where N represents any suitable whole number) may be arranged co-axially, in a stack, with their axes arranged in a direction that is at an oblique angle β that is neither parallel nor perpendicular to the axis A of the cap 44. Accordingly, each of the stacks of disc-shaped magnets in FIGS. 8-10 can selectively provide any one of multiple different magnetic signal magnitudes, depending upon the number and strength of the disc-shaped magnets in the stack.

More specifically, the disc-shaped magnets in a stack arrangement, such as shown in FIGS. 8, 9 and 10, provide a detectable magnetic field or signal having detectable parameters that are dependent, at least in part, on the number of disc-shaped magnets in the stack and the orientation of the magnetic poles of the disc-shaped magnets in the stack. The magnitude or strength of the magnetic field provided by each disc-shaped magnet affects the overall magnitude of the magnetic field provided by the stack or stacks of disc-shaped magnets. In addition, the number of disc-shaped magnets in the stack can affect and determine the magnitude of the detectable magnetic field provided by the stack of disc-shaped magnets. Typically, a stack having a greater number of disc-shaped magnets will provide a greater magnetic field magnitude as compared to a stack having a fewer number of disc-shaped magnets. The angle of the disc axis $A_c$, (relative to the cap axis A) may correspond to (be the same as or determine) the angle of the magnetic field provided by the stack, and is determined, in part, by the orientation of the magnetic poles of the disc-shaped magnets in the stack (whether parallel, perpendicular or obliquely angled relative to the cap axis A).

Accordingly, in particular examples, the number of disc-shaped magnets or the angle of the axis $A_c$ is selected to provide a desired or definable magnetic field (a definable magnetic signature or signal). Alternatively or in addition, the angle of magnet field relative to the cylindrical axis $A_c$ of the disc is selected to, at least partially, determine the desired or definable magnetic field (a definable magnetic signature or signal). Accordingly, each cap 44 may include one or more detectable features that provide a detectable magnetic field signal or signature that is dependent, at least in part, on one or more of: (a) the number of disc-shaped magnets in the stack; (b) the number of stacks of magnets in the detectable feature; (c) the magnitude of the magnetic signal provided by each disk-shaped magnet; (d) the orientation of each stack (such as perpendicular, parallel or obliquely angled relative to the cap axis A); and (e) the angle of magnetization of each disc-shaped magnets in each stack.

In certain examples, a plurality of different respective caps 44 with different respective values of one or more of the parameters (a)-(e), above, can be readily distinguished from one another, based on such detectable parameters. In certain examples, a plurality of pre-defined combinations of values for one or more of the parameters (a)-(e) may be associated with a corresponding plurality of pre-defined characteristics (characteristics of one or more of the cap, reservoir, infusion set, or infusion pump device, or components thereof). In that regard, the detection of a particular combination of values for the one or more parameters (a)-(e) corresponds to a detection of a cap (or reservoir, infusion set or infusion pump device) having the pre-defined characteristics associated with that combination of parameters. In certain examples, each respective cap 44 may have a unique magnetic field signature relative to each other cap 44. In other examples, each respective cap 44 may be part of a group of caps 44, where each cap in the group has corresponding, similar or identical characteristics, where each cap 44 in that group may have a common magnetic field signature that is unique to that group, relative to other groups of caps having other characteristics).

In the examples in FIGS. 4-7, the receptacle 60 has a trough-shaped recess having a shape of a partial-cylinder or semi-cylinder having its axis oriented in a direction transverse or perpendicular to the direction of the axis A of the cap 44. The receptacle 60 is configured to receive and retain one or more (or a plurality of) disc-shaped magnets, stacked or arranged side-by-side, with their cylindrical axes $A_c$ arranged in a direction that is perpendicular to (or generally perpendicular to) the direction of the axis A of the cap 44 (corresponding to the orientation of the stack of disc-shaped magnets $70_1$-$70_N$ in FIG. 8). In the examples shown in FIGS. 2-7, the cylindrical axis of the trough-shaped recess extends, generally, in a circumferential direction relative to the axis A of the cap 44 (or direction generally tangent to that circumferential direction). In other examples, the cylindrical axis of the trough-shaped recess extends in a radial direction relative to the axis A, or in a direction that is oblique to that radial direction.

On the other hand, the receptacle 62 has a cylindrical shape having its axis in a direction parallel to (or generally parallel to) the direction of the axis A of the cap 44. The receptacle 62 is configured to receive and retain one or more (or a plurality of) disc-shaped magnets, arranged in a stack, with their cylindrical axes $A_c$ arranged in a direction that is parallel to (or generally parallel to) the direction of the axis A of the cap 44 (corresponding to the orientation of the stack of disc-shaped magnets $70_1$-$70_N$ in FIG. 9). In further examples, a receptacle similar to the receptacle 62 (having a cylindrical shape) may be arranged with its cylindrical axis in a direction that is at an oblique angle relative to the axis A of the cap 44 (for example, corresponding to the orientation of the stack of disc-shaped magnets $70_1$-$70_N$ in FIG. 10).

While the examples in FIGS. 4-7 include a single trough-shaped receptacle 60 and a single cylindrical-shaped receptacle 62, other examples may include a plurality of trough-shaped receptacles 60 or a plurality of cylindrical-shaped receptacles 62 (or a combination of a plurality of each), located at any suitable location (or locations) on the surface $44_c$ or on other suitable locations on the cap 44. In some examples, the cap 44 may include one or more trough-shaped receptacles 60, or one or more cylindrical-shaped receptacles 62, or any suitable combination of one or more of each of the receptacles 60 or 62. In particular examples, the number and orientation of the receptacles is selected for each cap 44 (or each group of caps 44 having similar characteristics), to receive a particular number of disc-shaped magnets and to hold the disc-shaped magnets in one or more particular orientations, and to provide a particular, detectable magnetic field (magnetic signature or signal).

In the examples of FIGS. 4-7, each of the receptacles 60 and 62 is configured to receive and hold up to two disc-shaped magnets $70_1$ and $70_2$. In other examples, one or each receptacle 60 and 62 is configured to receive and hold no more than a single disc-shaped magnet, or to hold more than two disc-shaped magnet. In some examples, one or both receptacles 60 and 62 are configured to hold up to three disc-shaped members, or up to four disc-shaped members, or up to five disc-shaped members, or more.

Figure 5:
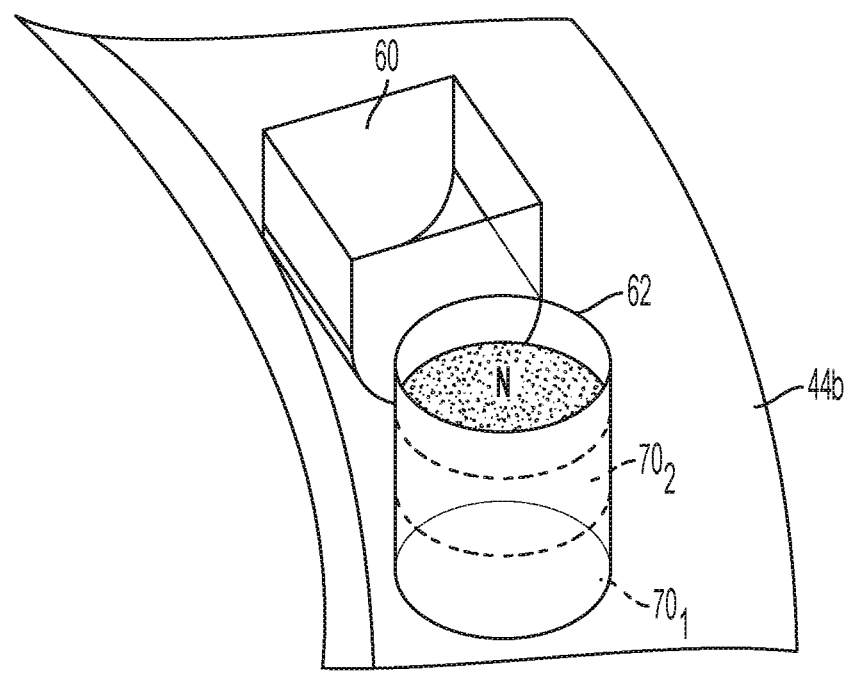
FIG. 5 is a partial bottom, perspective view of the cap of the embodiment of FIG. 2, including the detectable feature in a second configuration.
Figure 6:
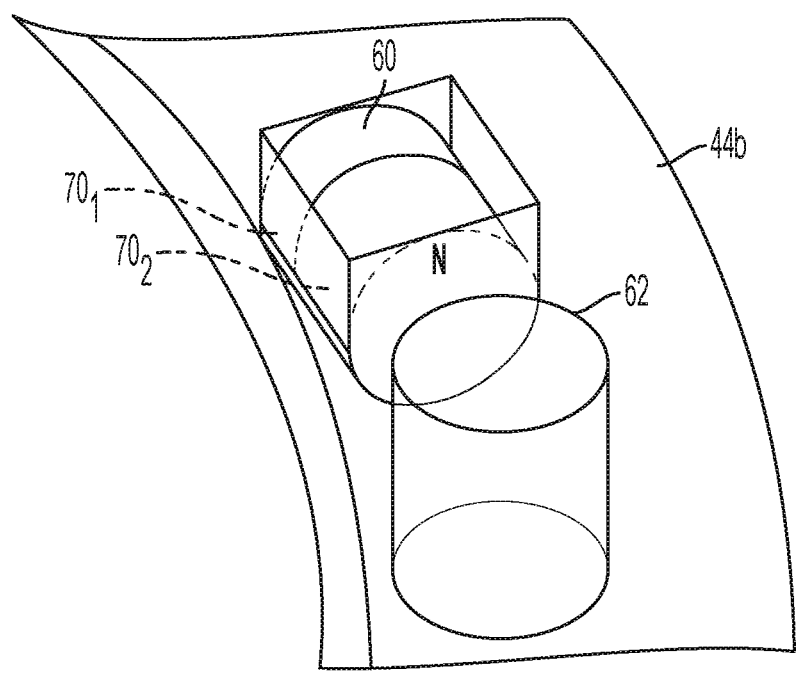
FIG. 6 is a partial bottom, perspective view of the cap of the embodiment of FIG. 2, including the detectable feature in a third configuration.
Figure 7:
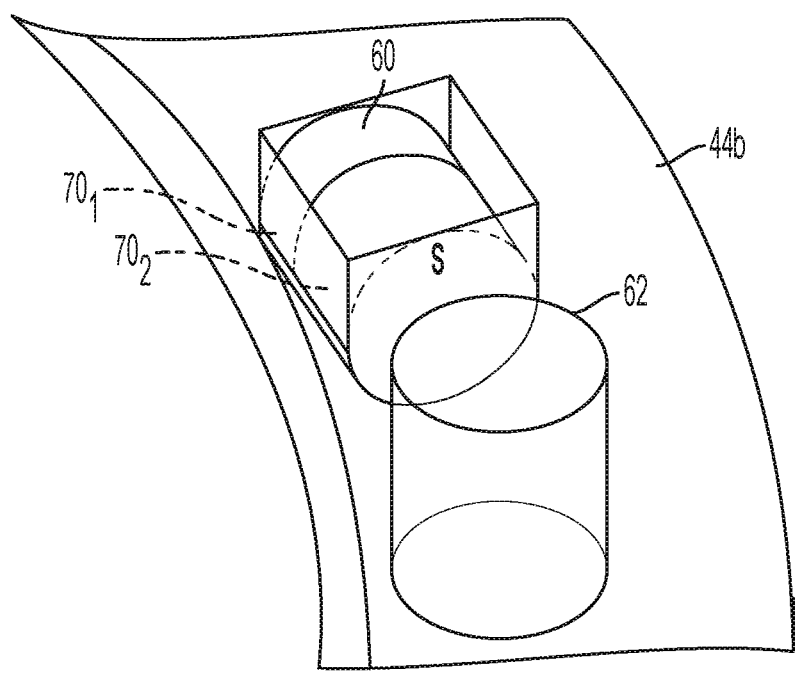
FIG. 7 is a partial bottom, perspective view of the cap of the embodiment of FIG. 2, including the detectable feature in a fourth configuration.

As shown in the examples in FIGS. 4-7, a single trough-shaped receptacle 60 and a single cylindrical-shaped receptacle 62 can hold one, two (or more) disc-shaped magnets $70_1$ and $70_2$ in various different orientations, where each orientation provides a different detectable magnetic field signature or signal relative to each other orientation. For example, in FIG. 4, two disc-shaped magnets $70_1$ and $70_2$ are arranged in a stack within the cylindrical-shaped receptacle 62 (with their cylindrical axes $A_c$ arranged in a direction parallel to the axis A of the cap 44), and with their respective north poles facing downward. In FIG. 5, the two disc-shaped magnets $70_1$ and $70_2$ are arranged in a stack within the cylindrical-shaped receptacle 62 (with their cylindrical axes $A_c$ arranged in a direction parallel to the axis A of the cap 44), and with their respective north poles facing downward. In FIG. 6, the two disc-shaped magnets $70_1$ and $70_2$ are arranged in a stack within the trough-shaped receptacle 62 (with their cylindrical axes $A_c$ arranged in a direction perpendicular to the axis A of the cap 44), and with their respective north poles facing outward relative to the plane of the page. In FIG. 7, the two disc-shaped magnets $70_1$ and $70_2$ are arranged in a stack within the trough-shaped receptacle 62 (with their cylindrical axes $A_c$ arranged in a direction perpendicular to the axis A of the cap 44), and with their respective north poles facing inward relative to the plane of the page.

Due to the different orientations of the disc-shaped magnets $70_1$ and $70_2$ in the different respective drawings of FIGS. 4-7, the detectable magnetic signature or signal provided by the detectable features in FIGS. 4-7 will differ relative to each other. In this manner, each different orientation of the disc-shaped magnets $70_1$ and $70_2$ may be associated with a different characteristic value (such as, but not limited to a value corresponding to a type of insulin in the reservoir 20, a length or diameter of the tubing 52, or other characteristic as discussed herein). Thus, as a non-limiting example, the orientation shown in FIG. 4 may correspond to one or more of those characteristic values (such as, but not limited to a first particular tubing length), while the orientations shown in FIGS. 5, 6 and 7 may correspond to one or more other values of the characteristic (such as, but not limited to second, third and fourth particular tubing lengths).

In the examples shown in FIGS. 4-7, two receptacles 60 and 62 and two disc-shaped magnets can provide a variety of different possible orientations and, thus, a variety of different possible detectable magnetic signatures. Accordingly, a plurality of caps 44 may be configured with the same arrangement of two receptacles 60 and 62, yet be loaded with different arrangements of disc-shaped magnets to provide different detectable signals. In other examples, a plurality of caps 44 may be configured with other suitable receptacle shapes and arrangements (but having a common or identical receptacle arrangement among the multiple caps) for receiving disc-shaped magnets in one of multiple possible orientations. Therefore, in particular examples, the cost of manufacture of multiple caps having a variety of different detectable signatures can be reduced or minimized, by employing a common receptacle arrangement among the multiple caps, but loading the receptacles of the different respective caps with disc-shaped magnets in different respective arrangements.

For example, the same two receptacles 60 and 62 and two disc-shaped magnets can be arranged in any one of the four different configurations in FIGS. 4-7, respectively, to provide any one of four distinctly different detectable signatures or signals. In further examples, additional different detectable signatures (distinguishable from the detectable signatures discussed above with regard to FIGS. 4-7) may be provided by selectively reducing the number of disc-shaped magnets received in the receptacles to be no more than one disc-shaped magnet. Accordingly, by selectively choosing either one or two disc-shaped magnets and by selecting one of the arrangements shown in FIGS. 4-7, any one of up to eight different distinctly detectable signatures or signals can be provided.

In further examples, yet additional different detectable signatures (distinguishable from the detectable signatures discussed above with regard to FIGS. 4-7) may be provided by providing receptacle 60 and 62 that are of sufficient size to receive and hold up to three (or other defined number) of disc-shaped magnets. Accordingly, by selectively choosing either one, two or three (or more) disc-shaped magnets and by selecting one of the orientation arrangements shown in FIGS. 4-7, yet additional distinctly detectable signatures or signals can be provided.

In the above-described examples, while the cap 44 is provided with two (or more) receptacles 60 and 62, only one of the receptacles receives and holds a selected number and polar orientation of disc-shaped magnets. However, in additional embodiments, yet further different detectable signatures (distinguishable from the detectable signatures discussed above with regard to FIGS. 4-7) may be provided by selectively loading both of the two receptacles 60 and 62 with one, two or more disc-shaped magnets in any of the arrangements described herein. Therefore, an arrangement of the same two receptacles 60 and 62 (but where each receptacle is sufficiently large to receive and hold more than two disc-shaped magnets) can provide many distinctly different detectable signatures or signals, depending upon the number and arrangement of disc-shaped magnets within the receptacles. In further examples that include more than two receptacles, yet additional distinctly different detectable signatures or signals may be selectively provided, depending upon the number and arrangement of disc-shaped magnets within the multiple receptacles.

Therefore, by providing the same (or a common) arrangement of one, two or more receptacles in a plurality of caps 44, the receptacles of each cap 44 (or of each group of plural caps 44) may be loaded with a different arrangement of disc-shaped magnets relative to each other cap (or relative to each other group of caps) to provide a detectable magnetic signature signal that is detectably different from the signal provided by each other cap (or by the caps in each other group of caps). Each different detectable signal may be associated with a corresponding different characteristic or characteristic value, as described herein, such that detection of the detectable signal corresponds to detection of the associated characteristic or characteristic value.

In particular examples, each of the receptacles 60 and 62 is configured to receive and hold one or more (or multiple) disc-shaped magnets of the same type, shape, size, such that the same disc-shaped magnets can be arranged in either one of the receptacles 60 and 62. In particular examples, the receptacles 60 and 62 are configured to receive and hold disc-shaped magnets that are of a type that are readily available and relatively inexpensive, which can reduce or minimize manufacturing costs. The use of a disc-shaped magnets that can be selectively arranged in multiple different stack arrangements and orientations to provide different detectable signals can simplify manufacturing inventory needs, by avoiding the need to keep an inventory of multiple detectable features having mutually different detectable parameters. In other examples, the disc-shaped magnets may have any suitable shape or configuration, including customized shapes or configurations. In yet other examples, magnet members having other shapes (other than disc shapes) may be employed in addition to or as an alternative to disc-shaped magnets. Such other shapes may include, but are not limited to cube or cuboid shapes, polygonal cuboid shapes, spherical or semispherical shapes, or the like. In such other examples, the shape of the receptacles 60 and 62 may be configured to correspond to the shape of the magnet members, to allow the receptacles to receive one or more of such magnet members in one or more orientations as described herein.

In particular examples, each of the receptacles 60 and 62 is configured to receive and hold one or more (or multiple) disc-shaped magnets in a press-fitting or friction fitting manner. In such examples, the diameter of the cylindrical shape of the receptacles 60 and 62 is approximately the same as (or slightly smaller than) the diameter of each disc-shaped magnet, such that the disc-shaped magnets may be slid into or pressed into the receptacles during manufacture (or post manufacture processes), and are tightly held in place within the receptacle by a friction fit with the inner surface(s) of the receptacle. In certain examples, the friction fit is sufficient to hold the disc-shaped magnets in place on the cap 44, without the need for adhesives or additional securing mechanisms. However, in other examples, the diameter of the cylindrical shape of the receptacles 60 and 62 is larger than the diameter of each disc-shaped magnet, such that the disc-shaped magnets may easily slide into the receptacles. In any of those examples, the disc-shaped magnets may be secured within the receptacle 60 or 62 and to the cap 44 by swaging, glue or other adhesive material, solder, welding, heat staking, molding or the like.

As discussed above, the infusion pump device 30 includes one or more sensor elements 34 that are configured to detect the presence of the detectable feature or other parameters of the detectable feature, when in a sufficient proximity or location relative to the detectable feature. In examples in which the detectable feature is composed of one or more disc-shaped magnets as described herein, such sensor(s) may include, but are not limited to, magnetoresistance (MR), Anisotropic Magneto-Resistive (AMR), Hall effect, magnetic reed, or other sensor device that provides a detectable response to the presence or alignment (or both) of a magnet.

In yet other embodiments, the one or more detectable features 60 are one or more electrically conductive metal or other electrically conductive material that is inductively detectable by one or more inductive sensors, where the one or more sensor elements 34 include one or more inductive sensors. In such other embodiments, the electrically conductive members that are inductively detectable (by an inductive detector) need not be a magnet or magnetized. In such examples, one or more (or each) disc-shaped magnet (e.g., disc-shaped magnets $70_1$ and $70_2$) of the above-discussed examples may be replaced with a disc-shaped electrically conductive member such as, but not limited to, a metal disc or a conductive ceramic disc. In such examples, the one or more (or plurality of) disc-shaped electrically conductive members may be arranged in a variety of different possible orientations within one or more (or a plurality of) receptacles (such as receptacles 60 and 62 discussed herein), to provide a corresponding variety of different possible inductively detectable signatures in a manner similar to the disc-shaped magnets discussed herein. In such examples, the one or more (or plurality of) disc-shaped members may be made of one or more different metals or other materials selected to provide a definable detectable inductive signature, such that any one or more of the different disc-shaped members may be selected and used in the stack, to provide selected, different inductively detectable signatures.

Accordingly, in particular examples, the one or more detectable features includes one or more (or a plurality of) magnetically detectable magnetic features or one or more (or a plurality of) inductively detectable conductive features, or a combination of both magnetically detectable features and inductively detectable features, which are carried by the cap 44 at one or more predefined locations on or in the cap housing 45. Elements 34 may include one or more (or a plurality of) sensors at a predefined location in or adjacent the reservoir receptacle 32 of the infusion pump device 30. In particular embodiments, the elements 34 and 42 are arranged such that they come into alignment or proximity (or both) when the base/reservoir/cap unit is fully or properly received in the reservoir receptacle 32 of the infusion pump device 30. Various types and arrangements of detectable features and sensor elements that may be employed in examples described herein, are described in the above-cited U.S. Pat. No. 9,452,255.

According to embodiments described herein, when the cap 44 (or the corresponding reservoir/base/cap unit) is received in the infusion pump device 30, one or more sensors 34 on the infusion pump device 30 interact with the detectable features to detect a proper (or improper) coupling of the cap 44 (or of the reservoir/base/cap unit) with the infusion pump device 30. In yet further embodiments, the one or more sensors and detectable features interact in a manner to communicate certain information relating to a characteristic of one or more of the reservoir 20, reservoir contents, cap 44, infusion set 50 or infusion pump device 30.

For example, the sensor(s) and detectable feature(s) may interact in a manner such that the sensor(s) 34 and electronics 80 (FIG. 11) detect(s) the presence or position (or both) of the detectable feature or other parameters of the detectable feature, when the cap 44 is properly received or operatively coupled (or both) with the infusion pump device 30. As referenced herein, proper receipt or operative coupling corresponds to a position of the cap 44 (or base/reservoir/cap unit) at which the drive linkage 22 of the reservoir 20 is operatively engaged with the drive device in the infusion pump device 30. In other embodiments, proper receipt or operative coupling corresponds to another suitable, predefined position of the cap 44 (or base/reservoir/cap unit).

When the connection interface 40 is coupled to the reservoir 20 and the base/reservoir/cap unit is fully and properly received in the reservoir receptacle 32 of the infusion pump device 30 (as shown in FIG. 3), the detectable feature(s) in one or both of the receptacles 60 or 62 on the cap 44 is(are) in sufficient alignment or proximity (or both) with the sensor element(s) 34 to allow the sensor to detect the detectable feature(s). However, when the connection interface 40 is not coupled to the reservoir 20, or when the base/reservoir/cap unit is not fully or properly received in the reservoir receptacle 32 of the infusion pump device 30, the detectable feature(s) in one or both receptacles 60 and 62 is(are) not in sufficient alignment or proximity (or both) with the sensor element(s) 34, such that the sensor element(s) does not properly detect the at least one detectable feature.

Alternatively or in addition, one or more magnet and sensor elements as described above are employed to detect one or more other characteristics associated with the cap 44 or the base/reservoir/cap unit, infusions set 50 (or combinations or components thereof), in addition to or as an alternative to detecting presence in or proper connection with the infusion pump device 30. In various embodiments, such other characteristics include but are not limited to characteristics of the cap 44, reservoir 20 (or its contents), infusion set 50, connection interface 40, or any combination thereof.

Figure 11:
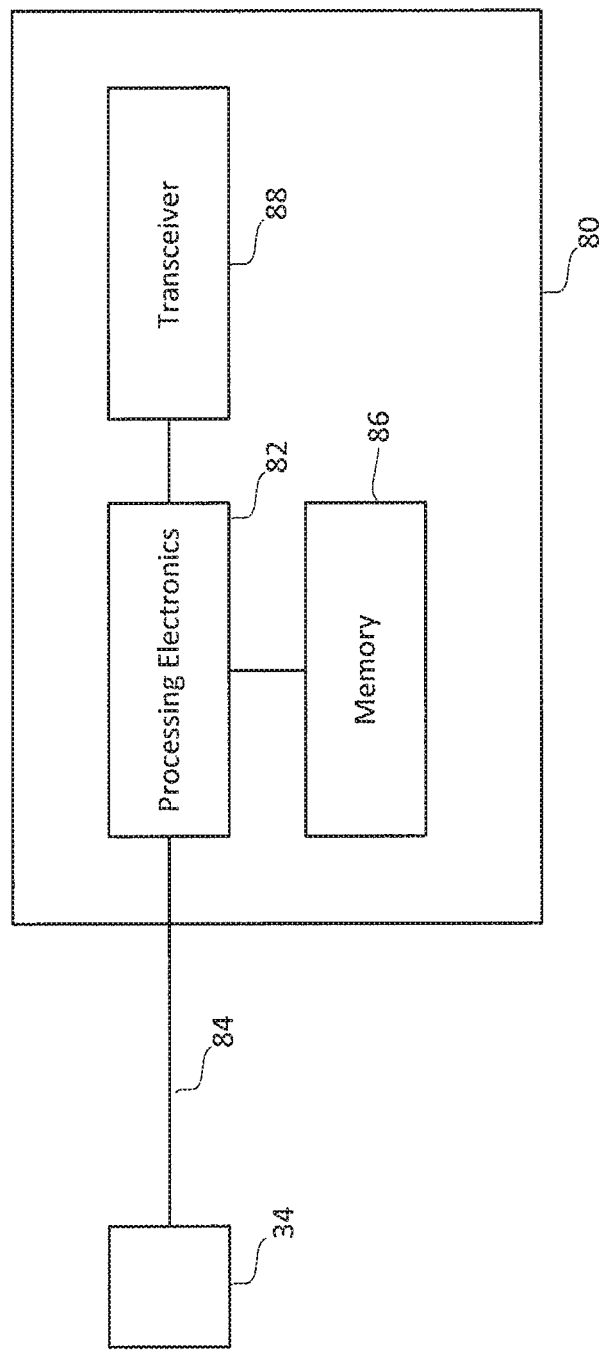
FIG. 11 is a schematic diagram of electronics associated with the infusion pump system of FIG. 1.

The electronics 80 in FIG. 11 include processing electronics 82 connected to receive electronic signals from the sensor, through a communication link 84. In one embodiment, the communication link 84 comprises one or more electrically conductive wires or traces or other electrically conductive material, wireless connection (such as, but not limited to radio frequency RF, Bluetooth, WiFi, inductive coupling, or other wireless communication link), or a combination thereof.

In particular embodiments, the processing electronics 82 includes one or more electronic processors configured to process information received from the sensor element 34. Such electronic processors may include, but are not limited to, a programmable general purpose processor, microprocessor, programmed or hardware configured special purpose processor, or the like, that is programmed with software, hardware, firmware, combinations thereof or otherwise configured to perform operations described herein. The electronics 80 includes one or more electronic memory devices 86 that stores data, programs or other software employed by the processing electronics 82 to perform operations described herein. In particular embodiments, the electronics 80 also includes a receiver, transmitter or transceiver 88, configured to receive, transmit, or both receive and transmit information from or to a further electronic device (not shown), such as, but not limited to, a user's computer, a health care entity's computer, or the like. The electronics 80 also includes or is connected with one or more power sources (not shown) for providing electrical power to the processing electronics 82 and, as needed, to the memory 86 and the transceiver 88. In particular embodiments in which the sensor element 34 requires electrical power, the above-noted power source(s) or a separate power source associated with the sensor element provides electrical power to the sensor element, for example, through the link 84 or through a separate electrical connection (not shown).

The processing electronics 82 is programmed or otherwise configured to process information received from the sensor element 34 and determine the presence or position of the cap 44 relative to the reservoir receptacle 32 of the infusion pump device 30 or other characteristics of the cap 44 (or base/reservoir cap unit), based on the particular parameters detected by the sensor element(s). In one example embodiment, the processing electronics 82 is configured to detect the presence or absence of a signal from the sensor element 34, to determine the presence or absence of the cap 44 in a predefined position relative to the reservoir receptacle 32. In other embodiments, the processing electronics 82 is configured to process a signal from the sensor element 34 to determine one or more parameters associated with the position of the cap 44, such as, but not limited to, the amount of rotation or linear displacement of the cap 44 relative to the reservoir receptacle 32, a rotational position of the cap 44 around the axis A, a linear position of the cap 44 along the dimension of the axis A, an angular position of the axis A of the cap 44 relative to the axis A of the reservoir receptacle 32, or any combination thereof.

In particular embodiments, the processing electronics 82 is configured to process a signal from the sensor element 34 to determine one or more other parameters associated with a characteristic of the cap 44, the reservoir 20 (or other component of the base/reservoir/cap unit), the infusion set, the infusion pump device 30, or the user. In certain embodiments, such characteristics may include, but are not limited to, the type or features of the infusion set that is connected to the cap 44. For example, a cap (or base/reservoir/cap unit) may be configured to connect with a variety of different infusion set products (such as, but not limited to the following infusion set products: Quickset® infusion set, Silhouette® infusion set, SureT® infusion set, Mio® infusion set, or the like). In addition, different infusion sets may be configured with a variety of different feature options for meeting user needs or preferences, such as, but not limited to, tubing length, cannula length and cannula type. In particular embodiments, different infusion sets, features and options may be associated with different respected detectable parameters of the detectable feature(s) and, thus, differentiated based on detected parameters of the detectable feature(s). In certain examples, electronics (such as electronics 80 in FIG. 11) may be configured to control operations of the infusion pump device, based on (or based in part on) detected parameters.

For example, once a parameter associated with a tubing length is detected, the infusion pump device 30 may automatically set a priming sequence that corresponds or is appropriate for the detected tubing length (and/or perform one or more other predefined tasks that depend or relate, at least in part, to the detected tubing length). Such embodiments can further automate infusion media delivery (such as, but not limited to insulin delivery), thus making therapy easier for the user.

In those embodiments, a particular characteristic may be associated with one or more detectable parameters of the detectable feature(s), where the detectable parameters include, but are not limited to one or more of: the existence of one or more magnet on the cap 44, the pattern or location of one or more magnets on the cap 44 (circumferential or linearly location relative to the dimension of the axis A), the magnitude or strength of the magnetic field of the detectable feature(s), the polarity direction of the detectable feature(s), magnetic field angle $\beta$, or the like.

Accordingly, in particular embodiments, each different characteristic of the reservoir 20, infusion set 50 or connection interface 40, is associated with a respectively different detectable parameter of the magnet. By reading the signature of the cap 44, the parameters that define the signature are detected. Accordingly, the processing electronics 82 may be configured to detect one or more detectable parameters of the magnet or sensor element; then determine one or more characteristics of the cap, base/reservoir/cap unit, reservoir, or infusion set based on the detectable parameter(s); and conduct one or more further predefined actions based on or using the determined characteristic(s).

Figure 12:
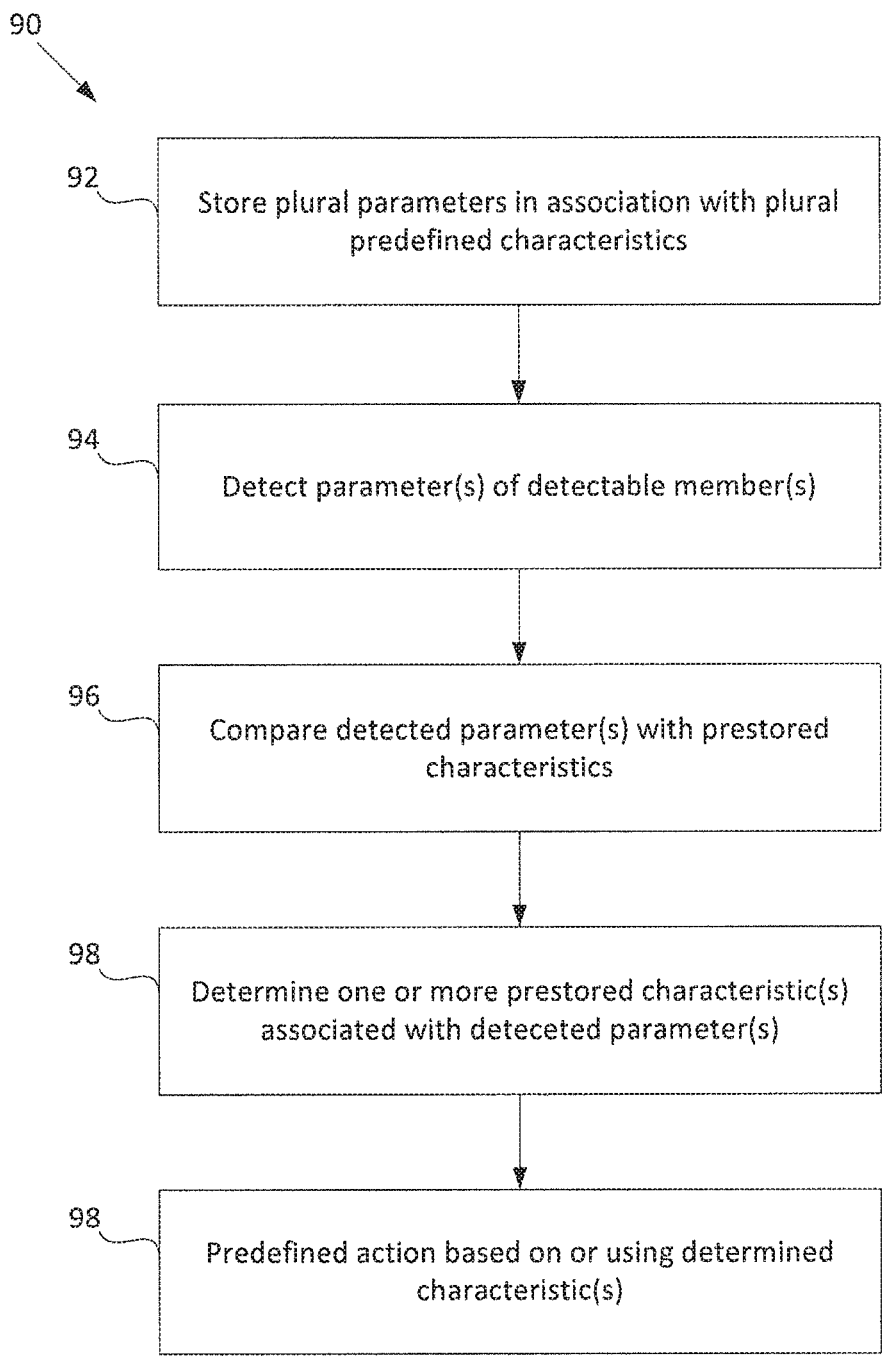
FIG. 12 is a flow chart of an example process carried out by processing electronics in the electronics of FIG. 11.

In particular embodiments, the electronics 80 (including the processing electronics 82) is configured to perform a process 90, such as explained with reference to the flowchart in FIG. 12. For example, in the process 90, a plurality of predefined parameters (parameters that could potentially be detected) are associated on a one-to-one basis (or other predefined association) with a corresponding plurality of characteristics of the cap 44, base/reservoir/cap unit, reservoir 20 or its contents, infusion set 50, connection interface 40, or any components or combination thereof. At 92, the associations of detectable parameters and the plurality of characteristics is stored in a memory, such as memory 86.

At 94 in the process 90, one or more parameters of one or more detectable features (e.g., disc-shaped magnets $70_1$, $70_2$, ... $70_N$) are detected by one or more sensor elements 34, for example, during or upon installation (or attempted installation) of a cap 44 or base/reservoir/cap unit in the infusion pump device 30. At 96, the processing electronics 82 compares information received from the sensor element(s) 34 with one or more pre-defined stored threshold values, or with information stored in a table (or stored in another data arrangement that associates a plurality of different detectable magnet locations or other magnet parameters with a corresponding plurality of characteristics, for example, but not limited to, a one-to-one correspondence of each different magnet location with a different characteristic, respectively). Alternatively or in addition, the processing electronics 82 may be configured to compare information received from the sensor element 34 with one or more thresholds or with information stored in a table or in another data arrangement that associates a plurality of different types of magnets (such as, but not limited to, magnets having different polarities, magnetic field angle ($\beta$, field strength, or a combination of the preceding) with a corresponding plurality of characteristics (for example, but not limited to, a one-to-one correspondence of each different magnet type with a different characteristic, respectively). In those embodiments, the processing electronics 82 is configured to determine the magnet location, the magnet type or both, based on one or more comparisons of information received from the sensor element 34 with the stored information. In particular embodiments, the stored table or other data arrangement is stored in the electronic memory 86.

Examples characteristics of the reservoir 20 (or its contents) include, but are not limited to, one or more of: the type or identity of the manufacturer of the reservoir 20 or components or contents thereof, the size of the reservoir 20, the type of infusion media in the reservoir 20 (such as, but not limited to the type of insulin, other drug or other media), the concentration of the infusion media in the reservoir 20, the volume amount of infusion media in the reservoir 20, a date (such as, but not limited to a date corresponding to an expiration date, fill date or other date related to the infusion media in the reservoir 20 or the reservoir 20 itself), a location (such as, but not limited to a location corresponding to the place where the reservoir 20, the cap 44, or infusion media in the reservoir 20 (or all) was made, filled, or otherwise processed, or a location for authorized use of the reservoir 20), a lot number (or other code associated with the batch in which the reservoir 20 or infusion media was made, cleaned, filled or otherwise processed), a serial number, a unique ID, a manufacture date, user identification information (for authorized users of the reservoir 20), or other predefined characteristic.

Example characteristics relating to the infusion set 50 connected to the cap 44 include, but are not limited to one or more of: the type or manufacturer of the infusion set 50 or components thereof, the length of the tubing 52, the diameter of the tubing 52, the length of the needle or cannula 56, the diameter of the needle or cannula 56, a date (such as, but not limited to a date corresponding to an expiration date, manufacturing date or assembly date of the needle or cannula 56), a location (such as, but not limited to a location corresponding to the place where the needle or cannula 56 was made or assembled with the housing 54, or a location for authorized use of the infusion set or components thereof), a lot number (or other code associated with the batch in which the infusion set 50 or components thereof was made, cleaned or otherwise processed), a cannula type, a needle type, a lot number, a serial number, a unique ID, user identification information (for authorized users of the infusion set 50), or other predefined characteristic.

Example characteristics relating to the connection interface 40 include, but are not limited to one or more of the type or manufacturer of the connection interface 40, cap 44, base 42 or components thereof, the length, diameter or other size dimension of the cap 44, a date (such as, but not limited to a date corresponding to an expiration date, manufacturing date or assembly date of the cap 44 or base 42), a location (such as, but not limited to a location corresponding to the place where the cap 44 or base 42 was made or assembled, or a location for authorized use of the cap 44 or base 42), a lot number (or other code associated with the batch in which the cap 44 or base 42 was made, cleaned or otherwise processed), a serial number, a unique ID, user identification information (for authorized users of the infusion set 50), or other predefined characteristic.

In particular embodiments, the processing electronics 82 is further configured to conduct one or more predefined actions at 99 in the process 90, based on or using the characteristics determined at 98 in the process 90. One or more predefined actions may include, but is not limited to determining one or more operational settings for the infusion pump device 30, based on one or more of the characteristics determined from detected parameters of the signals from the sensor element 34. In further examples of such embodiments, the processing electronics 82 also provides signals to the drive device or other components of the infusion pump device 30, to control operations of the drive device (or other components) based on one or more characteristics determined from the detected parameters. In one example, based at least in part on the detected parameter, the processing electronics 82 determines and sets operational settings for one or more of: pumping rate (amount of fluid pumped per unit time), pumping time period (amount of time of pumping), pumping power (amount of fluid pressure), priming (filling) the infusion set tubing 52, priming (filling) the infusion set needle or cannula 56, detecting an occlusion in the fluid path from the reservoir 20 to the infusion set needle or cannula 56, handling an occlusion (pumping time, pressure, or program for dislodging, compensating for, or otherwise handling an occlusion).

Thus, in one example, the detectable signature or signal from the detectable feature correspond to one or more characteristics relating to the particular type or size of infusion set 50 connected to the cap 44, where the detected characteristics are employed by the processing electronics 82 to determine a pumping rate or pumping time period (or both) that is sufficient to prime (fill) the infusion set tubing 52, or the needle or cannula 56 (or both). In another example, the detectable signature or signal from the detectable feature corresponds to one or more characteristics relating to the pumping time, pumping pressure or pumping program that is sufficient to dislodge or compensate for an occlusion in that particular type or size of infusion set 50.

In further embodiments, the processing electronics 82 is configured to perform (at 99 in the process 90) one or more other predefined actions based on or using the characteristic(s) determined at 98. Such other predefined actions may include, but are not limited to providing a control signal to deactivate or inhibit activation of a pump drive device in the infusion pump device 30, when the signal received from the sensor member 34 represents that the cap 44 or the base/reservoir/cap unit is not fully or properly received within the reservoir receptacle 32 of the infusion pump device 30. Alternatively or in addition, the processing electronics 82 is configured to provide a control signal to activate or allow activation of a pump drive device in the infusion pump device 30, when the signal received from the sensor member 34 represents that the cap 44 or the base/reservoir/cap unit is fully or properly received within the reservoir receptacle 32 of the infusion pump device 30.

Alternatively or in addition, the processing electronics 82 is configured to perform (at 99 in the process 90) yet one or more other predefined actions, such as, but not limited to providing an alarm signal, to activate an alarm indicator, when the signal received from the sensor member 34 represents that the cap 44 or the base/reservoir/cap unit is not fully or properly received within the reservoir receptacle 32 of the infusion pump device 30. In particular embodiments, the processing electronics 82 is configured to provide such an alarm or control signal (or both), only when the processing electronics 82 detects that the cap 44 or base/reservoir/cap unit is not fully and properly received within the reservoir receptacle 32, after having previously detected that the cap 44 or base/reservoir/cap unit is fully and properly received within the reservoir receptacle 32 (for example, indicating that a previously properly received cap 44 has since been moved or otherwise dislodged out of that position within the reservoir receptacle 32). In such embodiments, the processing electronics 82 may include (or be connected for communication with) a display device for displaying an alarm condition.

The alarm display device may include any suitable indicator such as, but is not limited to one or more of: a light emitting device, LED, LCD or other visual display device; a sound emitting device, speaker, buzzer or other audio display device; a vibrator, heater, or other tactile display device, or the like. In particular embodiments, the alarm display device is attached to or contained in the infusion pump device 30. In other embodiments, the alarm display device is attached to or contained in the cap 44. In yet other embodiments, the alarm display device is in an external device (such as, but not limited to a computer, smart phone, pager, or other electronic communication device) connected for communication with the electronics 80, for example, through a wired or wireless communication link.

In further embodiments, the processing electronics 82 is configured to perform (at 99 in process 90) other actions, such as, but not limited to recording data representing detected states or conditions (or characteristics) of one or more of the cap 44, base/reservoir/cap unit, and infusion pump device 30. In particular embodiments, the processing electronics 82 records such data in the electronic memory 86, in a form that can be retrieved by the processing electronics 82 or other processing electronics (not shown) at a time or date after recording. In such embodiments, the processing electronics 82 or other processing electronics may employ such data to generate reports, tables or other data structures for assisting with the evaluation of the recorded data. In yet further embodiments, the processing electronics 82 is configured to send such recorded data, reports, tables or other data structures to a predefined entity, for example, but not limited to, by transmitting the information through the transceiver 88. For example, in particular embodiments, the electronics 80 is configured to transmit recorded information to a remote facility at predefined or periodic intervals or upon receipt of such information from a sensor element.

In particular embodiments described above, the processing electronics 82 is configured to determine operational settings for the infusion pump device 30, provide alarm or control signals, record data or perform other predefined tasks base, at least in part, on detection of one or more detectable features (or information provided by a detectable parameter of the detectable feature(s)). In certain embodiments, the processing electronics 82 is configured to authenticate a base/reservoir/cap unit, cap 44 or reservoir 20, based on one or more of the parameters detected from the signals received from the sensor element 34. For example, the processing electronics 82 determines whether or not the detected parameters correspond to predefined characteristics associated with an authentic base/reservoir/cap unit, cap 44 or reservoir 20. In such embodiments, an authentic base/reservoir/cap unit, cap 44 or reservoir 20 may be for example, one that is authorized for use with the infusion pump device 30 by the manufacturer of at least one of the infusion pump device the base/reservoir/cap unit, cap 44, or reservoir 20. Alternatively or in addition, an authentic base/reservoir/cap unit, cap 44 or reservoir 20 may be one that is authorized by another predefined entity, such as, but not limited to, a government or industry standards or regulatory entity, or other predefined entity.

In certain embodiments, the processing electronics 82 coupled to the transceiver 88 may access, e.g., via a wired or wireless connection, directly or via another device(s), a database (e.g., on the Internet) to verify the authenticity of one or more of the base, reservoir, and/or cap using the serial number (unique ID, etc.) obtained from the base, reservoir, and/or cap, respectively, to confirm that such unit is authentic and genuine. Medical devices are stringently tested and heavily regulated, and use of unauthorized components may jeopardize proper treatment of the patient. Many of the components, such as the base/reservoir/cap, infusion set, etc., are single-use components, and the processing electronics 82 on the infusion pump device 30, e.g., may keep track of the serial numbers such that the patient is prohibited from re-using, purposefully or accidentally, a component where its safe useful life has already been depleted. Moreover, along with verifying authenticity, lot numbers, e.g., for the respective base, reservoir, and/or cap also may be checked against the database to ensure that no recalls are outstanding, and the user is alerted by (or even prohibited by) the infusion pump device 30 (or any other suitable device) to not use a particular base, reservoir, and/or cap and return it to the manufacturer if there is a recall underway, further enhancing the safety of the patient by using the most currently available information.

In particular embodiments, a detected geographic location, time or date (or any combination thereof) is included in the determination of authenticity. For example, the processing electronics 82 may be configured to determine that a base/reservoir/cap unit, cap 44 or reservoir 20 installed in the infusion pump device 30 is authentic, when the parameters detected from the signals received from the sensor element 34 correspond to characteristics that have been predefined (for example, pre-stored in memory 86) as an authentic base/reservoir/cap unit, cap or reservoir for use at a particular time, date or geographic location (or a combination thereof). In such embodiments, the memory 86 may store a table or other suitable data configuration that associates combinations of detectable magnet parameters and one or more dates, times and geographic locations (or any combination thereof) with an authentication determination. Examples of suitable tables are described in the above-cited U.S. Pat. No. 9,452,255.

In particular embodiments, the electronics 80 are configured to allow operation of the infusion pump device 30 when the processing electronics 82 determines that the base/reservoir/cap unit, cap 44 or reservoir 20 is authentic, and to not allow infusion operation of the infusion pump device 30 when the processing electronics 82 does not determine that the base/reservoir/cap unit, cap 44 or reservoir 20 is authentic. For example, the processing electronics 82 may be configured to provide a control signal to the drive device to stop operation of the drive device, or inhibit sending a drive or power signal to the drive device, or perform another predefined action to not allow dispensing of infusion media from the infusion pump device 30. In other embodiments, the electronics 80 is configured to allow an infusion operation (or a limited or other predefined infusion operation) of the infusion pump device 30, but to also performs one or more further predefined actions when the processing electronics 82 does not determine that the base/reservoir/cap unit, cap 44 or reservoir 20 is authentic. Such other predefined actions include, but are not limited to, one or more of providing a readable message on a display device of the infusion pump device 30, providing an alarm signal for operating an alarm indicator on the infusion pump device 30, and recording data associated with one or more of the infusion operation, the detected characteristic(s), time, date, and geographic location, or any combination thereof.

In further embodiments, the processing electronics 82 is configured to employ the detection of the parameters of the detectable feature(s) to determine presence or proper alignment, installation and connection of the base/reservoir/cap unit, cap 44 or reservoir 20 in the infusion pump device 30. In addition, detected parameters are associated (e.g. in a table or other manner, as discussed above) with one or more characteristics discussed herein. Then, once proper alignment, installation or connection of the base/reservoir/cap unit, cap 44 or reservoir 20 in the infusion pump device 30 is detected, the processing electronics controls operation of the infusion pump device 30 based on the one or more characteristics. The processing electronics 82 may be configured, in further embodiments, to determine the geographic location, time, date (or any combination thereof) at predefined times, periodically, randomly or the like, once the infusion pump device 30 has started operation.

In any of the above or further embodiments, the processing electronics 82 may be configured to record information regarding the infusion pump device 30, base/reservoir/cap unit, cap 44 or reservoir 20, or the usage and operation thereof. In particular embodiments, the processing electronics 82 is configured to record, for example, in the memory 86 data corresponding to one or more of identification information associated with the base/reservoir/cap unit, cap 44 or reservoir 20, dates or times of connection, operation or disconnection of the base/reservoir/cap unit, cap 44 or reservoir 20 to the infusion pump device 30, dates or times of alarm conditions, dates or times of operation of the infusion pump device 30, detected parameters or conditions associated with detected parameters. In further embodiments, the geographic location of the infusion pump device at the time of any of the above recording events is recorded as an alternative to or in addition to recording of date or time information. In such embodiments, recordings of usage of an infusion pump device 30, base/reservoir/cap unit, cap 44 or reservoir 20 outside of a predefined geographic region, date or time (for example, beyond a predefined expiration date) may be made. In further embodiments, as an alternative to or in addition to recording the event, the processing electronics 82 is configured to provide one or more of an alarm indication and a display of a warning message on a display device in the infusion pump device, upon the detection of usage of an infusion pump device 30, base/reservoir/cap unit, cap 44 or reservoir 20 outside of a predefined geographic region, date or time.

In further embodiments, one or more wireless or wired communication devices is provided on the infusion pump device 30 (or other delivery device) and is configured and controlled to transmit volume information relating to the volume of infusion fluid remaining in or dispensed from the reservoir 20 (or other information corresponding to detected parameters or associated characteristics) for display on another electronic device separate from or located remote from the infusion pump device 30. In particular embodiments, the wireless communication device(s) are configured to connect for communication on a communication network (such as, but not limited to the Internet), with one or more pre-defined network connected devices. Such one or more pre-defined network connected devices may be located at remote geographic locations relative to the infusion pump device 30 (or other delivery device). In particular embodiments, such network connected devices include a server configured to receive information from the infusion pump device 30 (or other delivery device) or from another network connected device (such as a cradle, user computer, or the like) that communicates with the infusion pump device 30 (or other delivery device). Such information may include, but is not limited to information corresponding to one or more detected parameters or one or more associated characteristics, or other information regarding the reservoir 20, cap 44, base/reservoir/cap unit or infusion set as described above.

In such embodiments, the network connected server may be associated with an entity that records information, supplies associated products such as refills or replacement parts, provides medical treatment or medical insurance to the user or the like. In one example, the network connected server is associated with the Carelink™ system of Medtronic Inc. In other embodiments, the network connected server is one or more other servers and associated entities. Accordingly, such information may be employed by the server (or associated entity) to determine whether or not (or when) to send refills, new or replacement reservoirs, caps, infusion set needle housings, infusion set tubing, or other components of the cap 44, base/reservoir/cap unit, or infusion set. In further embodiments, such information may be provided to the user's doctor or other medical treatment entity associated with the user (for tracking, diagnosing, adjusting treatment plans or other suitable uses). Thus, in such embodiments, refills or replacement components may be sent to users, automatically (without requiring the user to place an order), and usage information can be provided to the user's healthcare provider, insurance provider or other suitable entities, automatically.

In further embodiments, the network connected server is configured to provide (and the infusion pump device 30 or other delivery device is configured to receive) information through the above-noted network communication connection or other network connection. Such information may include, but is not limited to, instructions or recommendations for replacing or refilling a reservoir 20, cap 44, base/reservoir/cap unit or infusion set, messages or notices from healthcare providers, insurance carriers or manufacturers, recall notices or the like. In particular embodiments, electronics (such as electronics 80) in the infusion pump device 30 (or other delivery device) is configured to perform one or more predefined actions (as discussed above) in response to receipt of a predefined instruction, notice or message.

While the description above refers to particular embodiments of the present invention, it will be understood that many modifications may be made without departing from the spirit thereof. The accompanying claims are intended to cover such modifications as would fall within the true scope and spirit of the present invention. The presently disclosed embodiments are therefore to be considered in all respects as illustrative and not restrictive, the scope of the invention being indicated by the appended claims rather than the foregoing description, and all changes which come within the meaning and range of equivalency of the claims are therefore intended to be embraced therein.

We claim:

1. A connector interface system, comprising:
   a cap to connect to a reservoir to form a reservoir/cap unit for installation into an infusion pump device, the cap having at least one receptacle for receiving one or more detectable features; and
   at least one detectable feature comprising at least one disc-shaped member received within the at least one receptacle, for detection by at least one sensor element on the infusion pump device when the reservoir of the reservoir/cap unit is received in a reservoir receptacle of the infusion pump device;
   wherein the at least one detectable feature has at least one detectable parameter that is associated with one or more characteristics of the cap, the reservoir, the infusion pump device, a cannula associated with the cap or a tubing connected between the cap and the cannula;
   wherein the at least one receptacle comprises a plurality of receptacles, each receptacle configured for receiving one or more detectable features.

2. The connector interface system of claim 1, wherein the at least one detectable feature comprises a plurality of disc-shaped members arranged in a stack within the at least one receptacle.

3. The connector interface system of claim 1, wherein the at least one detectable feature comprises a plurality of disc-shaped members arranged in a stack within one of the at least one receptacle, while the other of the at least one receptacles is devoid of disc-shaped members.

4. The connector interface system of claim 1, wherein the at least one detectable feature comprises a plurality of disc-shaped members arranged in a stack within each of the plurality of receptacles.

5. The connector interface system of claim 1, wherein the cap and the reservoir have a common longitudinal axis A, and wherein the plurality of receptacles comprise a first receptacle having a partial cylindrical or semi-cylindrical configuration, having a cylindrical axis that extends in a direction transverse to the direction of the axis A.

6. The connector interface system of claim 1, wherein the plurality of receptacles comprise at least one receptacle having a cylindrical configuration with a cylindrical axis that extends in a direction that is parallel to or that is at an oblique angle relative to the direction of the axis A.

7. The connector interface system of claim 1, wherein the cap and the reservoir have a common longitudinal axis A, and wherein the plurality of receptacles comprise a first receptacle having a cylindrical configuration with a cylindrical axis that extends in a direction that is parallel to or that is at an oblique angle relative to the direction of the axis A.

8. The connector interface system of claim 1, wherein the at least one disc-shaped member comprises at least one disc-shaped magnet, and wherein the at least one detectable feature provides a detectable magnetic field.

9. The connector interface system of claim 8, wherein the cap and the reservoir have a common longitudinal axis A, and wherein the at least one detectable parameter comprises at least one of a magnitude of the magnetic field, a polarity direction of the magnetic field and an angle of the magnetic field relative to the axis A.

10. The connector interface system of claim 1, wherein the at least one disc-shaped member comprises a plurality of disc-shaped magnets, and wherein the detectable magnetic field is dependent on the number of disc-shaped magnets in the detectable feature, and wherein the number of disc-shaped magnets in the detectable feature is adjustable.

11. The connector interface system of claim 1, wherein the at least one disc-shaped member comprises at least one disc-shaped electrically conductive member, and wherein the at least one detectable feature provides an inductively detectable signature.

12. The connector interface system of claim 11, wherein the at least one disc-shaped member comprises a number of disc-shaped electrically conductive member, the number being greater than one, and wherein the inductively detectable signature is dependent on the number of disc-shaped members in the detectable feature, and wherein the number of disc-shaped members in the detectable feature is adjustable.

13. A connector interface system, comprising:
a cap to connect to a reservoir to form a reservoir/cap unit for installation into an infusion pump device, the cap having at least one receptacle for receiving one or more detectable features; and
at least one detectable feature comprising at least one disc-shaped member received within the at least one receptacle, for detection by at least one sensor element on the infusion pump device when the reservoir of the reservoir/cap unit is received in a reservoir receptacle of the infusion pump device;
wherein the at least one detectable feature has at least one detectable parameter that is associated with one or more characteristics of the cap, the reservoir, the infusion pump device, a cannula associated with the cap or a tubing connected between the cap and the cannula;
wherein the cap and the reservoir have a common longitudinal axis A, and wherein the at least one receptacle comprises a first receptacle having a partial cylindrical or semi-cylindrical configuration, having a cylindrical axis that extends in a direction transverse to the direction of the axis A; and
wherein the at least one receptacle comprises a second receptacle having a cylindrical configuration with a cylindrical axis that extends in a direction parallel to or at an oblique angle relative to the direction of the axis A.

14. A connector interface system, comprising:
a cap to connect to a reservoir to form a reservoir/cap unit for installation into an infusion pump device, the cap having at least one receptacle for receiving one or more detectable features; and
at least one detectable feature comprising at least one disc-shaped member received within the at least one receptacle, for detection by at least one sensor element on the infusion pump device when the reservoir of the reservoir/cap unit is received in a reservoir receptacle of the infusion pump device;
wherein the at least one detectable feature has at least one detectable parameter that is associated with one or more characteristics of the cap, the reservoir, the infusion pump device, a cannula associated with the cap or a tubing connected between the cap and the cannula; and
wherein the cap and the reservoir have a common longitudinal axis A, and wherein the at least one receptacle comprises a receptacle having a cylindrical configuration with a cylindrical axis that extends in a direction parallel to or at an oblique angle relative to the direction of the axis A.

15. A connector interface system, comprising:
a cap to connect to a reservoir to form a reservoir/cap unit for installation into an infusion pump device, the cap having at least one receptacle for receiving one or more detectable features; and
at least one detectable feature received within one of the at least one receptacle, the at least one detectable feature comprising a number of detectable members, the number being greater than one, wherein each detectable member has the same shape and size and is configured to be selectively received within the at least one receptacle, for detection by at least one sensor element on the infusion pump device when the reservoir of the reservoir/cap unit is received in a reservoir receptacle of the infusion pump device;
wherein the at least one detectable feature has at least one detectable parameter that is dependent, at least in part, on the number of detectable members received within the one of the at least one receptacle;
wherein the at least one detectable parameter is associated with one or more characteristics of the cap, the reservoir, the infusion pump device, a cannula associated with the cap or a tubing connected between the cap and the cannula; and
wherein each detectable member comprises a disc-shaped magnet that provides a detectable magnetic field.

16. The connector interface system of claim 15, wherein the one or more characteristics comprises one or more of: a type or identity of a manufacturer of the reservoir, or the cap; a size of the reservoir or the cap; a type or concentration of infusion media in the reservoir; a volume amount of infusion media in the reservoir; a date corresponding to a manufacturing date, expiration date or fill date related to infusion media in the reservoir; a date corresponding to a manufacturing date or expiration date of the reservoir or the cap; a location corresponding to a place where the reservoir or infusion media in the reservoir was made, filled, or otherwise processed; a location corresponding to a place where the cap was made, assembled or otherwise processed; a location corresponding to a place where the reservoir, infusion media in the reservoir or the cap is authorized to be used; a lot number or code associated with a batch in which the reservoir, the cap or infusion media was made, cleaned, filled or otherwise processed; a serial number; a unique ID; user identification information for authorized users; a type, length or size of a cannula associated with the cap; or a type, length or size of a tubing connected between the cap and the cannula.

17. A method of using a connector interface system, comprising:
connecting a cap to a reservoir to form a reservoir/cap unit for installation into an infusion pump device, the cap having at least one receptacle for receiving one or more detectable features; and
inserting at least one detectable feature comprising a number of disc-shaped members within the at least one receptacle, for detection by at least one sensor element on the infusion pump device when the reservoir of the reservoir/cap unit is received in a reservoir receptacle of the infusion pump device, the number of disc-shaped members being greater than one;
wherein the at least one detectable feature has at least one detectable parameter that is dependent, in part, on the number of disc-shaped members, wherein the at least one detectable parameter is associated with one or more characteristics of the cap, the reservoir, the infusion pump device, a cannula associated with the cap or a tubing connected between the cap and the cannula, and wherein the at least one detectable parameter comprises a magnet field signature or an inductively detectable signature; and wherein the at least one receptacle comprises a plurality of receptacles, each receptacle configured for receiving one or more detectable features.

\* \* \* \* \*